(12) United States Patent
Caroon et al.

(10) Patent No.: US 7,470,684 B2
(45) Date of Patent: Dec. 30, 2008

(54) SPIROPIPERIDINE DERIVATIVES AS NK3 ANTAGONISTS

(75) Inventors: Joanie Marie Caroon, Mountain View, CA (US); Michael Patrick Dillon, San Francisco, CA (US); Bo Han, Pudong (CN); Matthias Nettekoven, Grenzach-Wyhlen (DE); Hasane Ratni, Habsheim (FR); Walter Vifian, Olten (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/960,765

(22) Filed: Dec. 20, 2007

(65) Prior Publication Data

US 2008/0176839 A1   Jul. 24, 2008

(30) Foreign Application Priority Data

Jan. 3, 2007   (EP)   ................... 07100064

(51) Int. Cl.
  *C07D 498/10*   (2006.01)
  *A61K 31/537*   (2006.01)
(52) U.S. Cl. ..................... 514/230.5; 544/71
(58) Field of Classification Search ............ 544/71; 514/230.5
  See application file for complete search history.

(56) References Cited

FOREIGN PATENT DOCUMENTS

WO   WO 02/092604   11/2002
WO   WO 2005/092858   10/2005

OTHER PUBLICATIONS

Giardina Gam et al, *Expert Opin. On Therapeutic Patents*, (2000) 10:6, 939-960, XP002349355.
Tooney et al., Neurosci. Letters, 2000 vol. 283 pp. 185-188.
Giardina et al., Exp. Opin. Ther. Patents 2000, vol. 10, pp. 939-930.
Jung et al., Neuroscience, 1996, vol. 74 pp. 403-414.
Marco et al., Neuropeptides, 1998 vol. 32, pp. 481-488.
Stoessl et al., 1989, Neurosci. Letters, 1987, vol. 80(3) pp. 321-326.
Millan et al., Psychopharmacology vol. 14, 2000 pp. 114-138.
Panocka et al., Peptides, 2001, vol. 22(7) pp. 1037-1042.
Ribeiro et al., Neurosci. Letters, 1998, vol. 258(3) pp. 155-158.
Knapp et al., Br. J. Psychiatry, 2002, vol. 18, pp. 19-23.
Kameyama et al., Methods Find Exp. Clin. Pharmacol., 1998 vol. 20(7) pp. 555-560.
Clark et al., Journal of Medicinal Chemistry (1983) vol. 26(5) pp. 657-661.

*Primary Examiner*—Kahsay T Habte
(74) *Attorney, Agent, or Firm*—George W. Johnston; Patricia S. Rocha-Tramaloni; Kimberly J. Prior

(57) ABSTRACT

The present invention relates to a compound of formula I

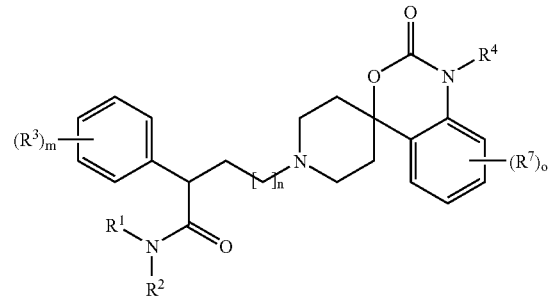

wherein $R^1$, $R^2$, $R^3$, $R^4$, $R^7$, m and n are as defined herein. These compounds are high potential NK-3 receptor antagonists useful for the treatment of depression, pain, psychosis, Parkinson's disease, schizophrenia, anxiety and attention deficit hyperactivity disorder (ADHD).

31 Claims, No Drawings

SPIROPIPERIDINE DERIVATIVES AS NK3 ANTAGONISTS

PRIORITY TO RELATED APPLICATION(S)

This application claims the benefit of European Patent Application No. 07100064.0, filed Jan. 3, 2007, which is hereby incorporated by reference in its entirety.

BACKGROUND OF THE INVENTION

The three main mammalian tachykinins, substance P(SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters*, 2000, 283, 185-188; *Exp. Opin. Ther. Patents* 2000, 10, 939-960; *Neuroscience*, 1996, 74, 403-414; *Neuropeptides*, 1998, 32, 481-488).

Neurokinin 3 receptors are expressed in the brain and strategically located along with NKB, i.e. its natural substrate, in noradrenergic and dopaminergic pathways. Indeed, CNS administration of senktide, a peptide agonist of NK-3 receptors, increases noradrenaline and dopamine in brain areas such as the prefrontal cortex. NK-3 receptors are less abundant in serotonergic pathways, nevertheless, intracerebroventricular administration of senktide elicits behavioural manifestations of serotonergic stimulation, such as forepaw treading, that were blocked by serotonin depletion (Stoessl et al., 1989, *Neurosci. Letters*, 1987, 80(3), 321-6).

Thus, activation of NK-3 receptors stimulates noradrenergic, dopaminergic and serotonergic systems, i.e., those that are critically involved in the anti-depressant and anxiolytic effects of SSRI's (serotonin re-uptake inhibitors) and SNRI's (serotonin noradrenaline re-uptake inhibitors (Millan et al., *Psychopharmacoogy* 14 (2000), 114-138). Indeed, preliminary mice studies suggest that intraperitoneal administration of the NK-3 agonist aminosenktide exhibits anti-depressant-like effects in the forced swimming test (Panocka et al., *Peptides*, 2001, 22(7), 1037-42), and that intracerebroventricular administration of senktide exhibits anxiolytic-like effects in the elevated plus maze (Ribeiro and De Lima, *Neurosci Letters*, 1998, 258(3), 155-8).

In addition, because cognitive impairment may be an important element of these diseases (Knapp et al., *Br J Psychiatry*, 2002, 18, 19-23), it is of great interest that senktide, after its local administration in the area of cholinergic cell bodies (septal area) stimulates acetylcholine in the hippocampus. Indeed, senktide ameliorates the scopolamine-induced impairment in a cognition test (Kameyama et al., *Methods Find Exp Clin Pharmacol.*, 1998, 20(7), 555-60).

In conclusion, based on biochemical and behavioral data, activation of NK-3 receptors is expected to lead to anti-depressant and anxiolytic-like effects, and in addition, to ameliorate possible cognitive deficits for the treatment of anxiety, depression, bipolar disorders, Parkinson's disease, schizophrenia and pain.

SUMMARY OF THE INVENTION

The present invention provides a compound of formula I

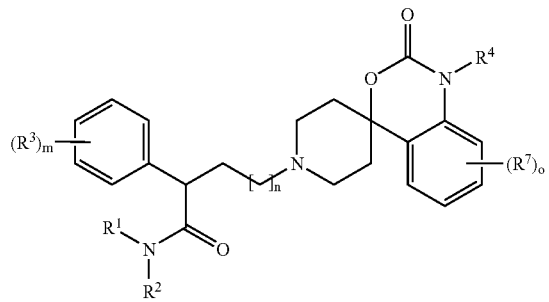

wherein
R$^1$ is hydrogen or lower alkyl;
R$^2$ is lower alkyl, lower hydroxyalkyl or —(CHR$^5$)$_x$-A;
  R$^5$ is hydrogen, lower alkyl, lower hydroxyalkyl, or heteroaryl optionally substituted by lower alkyl;
  A is a cycloalkyl, aryl, heterocyclyl or heteroaryl ring, which rings are optionally substituted by one or more R$^6$, wherein R$^6$ is lower alkyl, lower alkoxy, lower alkylsulfonyl, cyano, halogen, lower alkyl substituted by halogen or lower alkoxy substituted by halogen, or is aryl, heterocyclyl or heteroaryl optionally substituted by lower alkyl or is cycloalkyl optionally substituted by lower alkyl;
  x is 0, 1, 2 or 3;

or R$^1$ and R$^2$ together with the N-atom to which they are attached form a heterocyclyl or heteroaryl ring, which rings are optionally substituted by one or more substituents selected from the group consisting of lower alkyl, lower alkoxy, lower alkylsulfonyl, halogen, cycloalkyl, benzyl and aryl;
R$^3$ is hydrogen or halogen;
R$^4$ is hydrogen or lower alkyl;
R$^7$ is hydrogen, halogen or lower alkyl;
m is 1 or 2; when m is 2, each R$^3$ can be the same or different;
n is 1 or 2;
o is 1 or 2; when o is 2, each R$^7$ can be the same or different;

or to a pharmaceutically suitable acid addition salt thereof.

The invention includes all stereoisomeric forms, including individual diastereoisomers and enantiomers of the compound of formula (I) as well as racemic and non-racemic mixtures thereof.

The invention also provides pharmaceutical compositions which contain a compound of the invention and a pharmaceutically acceptable carrier. The invention further provides methods for the manufacture of the compounds and compositions of the invention.

Compounds are high potential NK-3 receptor antagonists for the treatment of depression, pain, psychosis, Parkinson's disease, schizophrenia, anxiety and attention deficit hyperactivity disorder (ADHD). Furthermore, the compounds have good activity toward the NK-1 and the NK-2 receptors.

The invention provides methods for the treatment of depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. The preferred indications using the compounds of the present invention are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain alkyl group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower hydroxyalkyl" denotes an alkyl group as defined above, wherein at least one hydrogen atom is replaced by hydroxyl. Preferred lower hydroxyalkyl groups are groups with 1-4 carbon atoms and having one hydroxyl.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "lower alkoxy" denotes a group wherein the alkyl residue is as defined above and which is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes a group wherein the alkyl residue is as defined above "lower alkyl substituted by halogen" and which is attached via an oxygen atom. Preferred lower alkoxy substituted by halogen groups are groups having 1-4 carbon atoms.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclopentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, benzyl, naphthyl or indanyl. Preferred is the phenyl group.

The term "heteroaryl" denotes a cyclic aromatic hydrocarbon radical consisting of one or more fused rings containing 3-14 ring atoms, preferably containing 5-10 ring atoms, in which at least one ring is aromatic in nature, and which contains at least one heteroatom, selected from N, O and S, for example dihydroisoquinolinyl, pyrazinyl, pyrazolyl, pyridinyl, pyridyl, pyrimidyl, oxadiazolyl, triazolyl, tetrazolyl, thiazolyl, thiadiazolyl, thienyl, furyl or imidazolyl. Preferred heteroaryl group is dihydroisoquinolinyl, furyl, pyrazolyl, pyridinyl, thiadiazolyl, thienyl or imidazolyl.

The term "heterocycle" denotes non-aromatic ring or a ring system containing 3-14 ring atoms, preferrably containing 5-6 ring atoms, wherein at least one ring atom is N, O or S, for example, pyrrol-1-yl, piperidin-1-yl, piperazin-1-yl, morpholin-4-yl, thiomorpholin-4-yl, 1-oxo-thiomorpholin-4-yl or 1,1-dioxo-thiomorpholin-4-yl. Preferred heterocycle group is piperizin-1-yl or morpholin-4-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following groups of compounds of formula (I) are preferred:

A compound wherein one of $R^1$ or $R^2$ is lower alkyl. The following compounds relate to this group.

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

A compound wherein one of $R^1$ or $R^2$ represents —$(CHR^5)_x$-A, where A is aryl or heteroaryl and X is 1. The following compounds relate to this group.

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-4-(6-fluoro-2-oxo-1,2-dihydro-1'H-spiro[3,1-benzoxazine-4,4'-piperidin]-1'-yl)-2-(4-fluorophenyl)butanamide;

4-(6-fluoro-2-oxo-1,2-dihydro-1'H-spiro[3,1-benzoxazine-4,4'-piperidin]-1'-yl)-2-(4-fluorophenyl)-N-[2-(trifluoromethoxy)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

4-(6-fluoro-2-oxo-1,2-dihydro-1'H-spiro[3,1-benzoxazine-4,4'-piperidin]-1'-yl)-2-(4-fluorophenyl)-N-[3-(trifluoromethyl)benzyl]butanamide;

N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-[(4-chlorophenyl) (1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;
2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;
2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;
2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;
2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;
2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;
N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;
2-(3,4-dichlorophenyl)-5-(6-fluoro-2-oxo-1,2-dihydro-1'H-spiro[3,1-benzoxazine-4,4'-piperidin]-1'-yl)-N-[(3-methyl-2-thienyl)methyl]pentanamide;
2-(3,4-dichlorophenyl)-5-(6-fluoro-2-oxo-1,2-dihydro-1'H-spiro[3,1-benzoxazine-4,4'-piperidin]-1'-yl)-N-[2-(trifluoromethoxy)benzyl]pentanamide;
N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide;
2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide;
N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl) pentanamide;
2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide;
2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide;
2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)pentanamide;
2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethyl)benzyl]pentanamide;
2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide;
(2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride;
(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;
(2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

A compound wherein $R^1$ and $R^2$ together with the N-atom to which they are attached form a heterocyclyl or heteroaryl ring, which rings are substituted by one or more halogen. The following compounds relate to this group.

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one; and
1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one.

A compound wherein $R^3$ is halogen. More preferably, a compound wherein $R^3$ is chlorine and m is 2. The following compounds relate to this group.

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;
N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;
N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;
2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide;
2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;
N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;
N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;
N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;
2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-5-(6-fluoro-2-oxo-1,2-dihydro-1'H-spiro[3,1-benzoxazine-4,4'-piperidin]-1'-yl)-N-[(3-methyl-2-thienyl)methyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-[2-(trifluoromethoxy)benzyl]pentanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)pentanamide;

2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethyl)benzyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide;

(2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

A compound, wherein $R^4$ is lower alkyl. The following compounds relate to this group.

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

A compound, wherein n is 1. The following compounds relate to this group.

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-4-(6-fluoro-2-oxo-1,2-dihydro-1'H-spiro[3,1-benzoxazine-4,4'-piperidin]-1'-yl)-2-(4-fluorophenyl)butanamide;

4-(6-fluoro-2-oxo-1,2-dihydro-1'H-spiro[3,1-benzoxazine-4,4'-piperidin]-1'-yl)-2-(4-fluorophenyl)-N-[2-(trifluoromethoxy)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

4-(6-fluoro-2-oxo-1,2-dihydro-1'H-spiro[3,1-benzoxazine-4,4'-piperidin]-1'-yl)-2-(4-fluorophenyl)-N-[3-(trifluoromethyl)benzyl]butanamide;

N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;
2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;
N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;
(2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride;
(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and
(2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process described below, which process comprises reacting a compound of formula

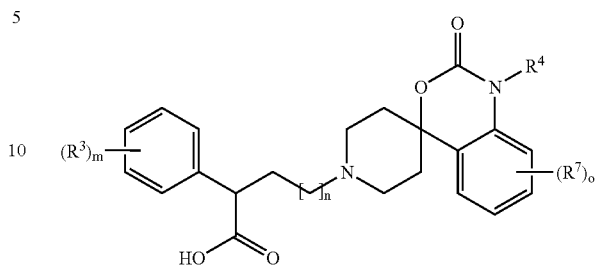

VIII with an amine of formula

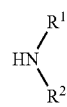

IX wherein the substituents have the same meanings as described before, under coupling conditions to provide the spiropiperidine derivatives of formula

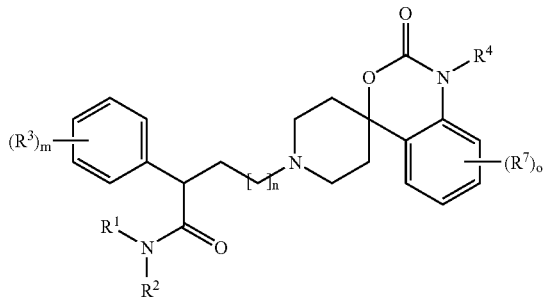

I and, if desired, converting a compound of formula I into a pharmaceutically acceptable salt.

Scheme 1

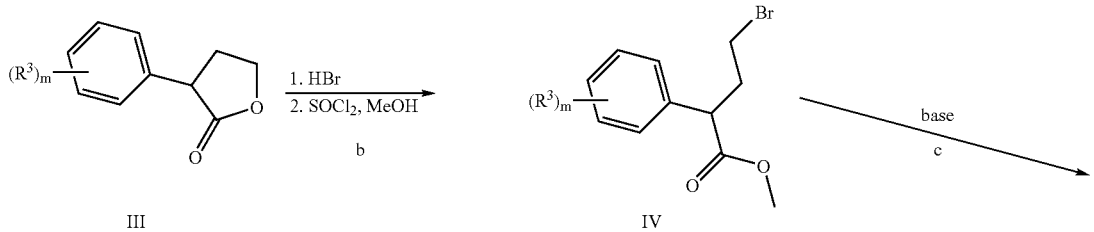

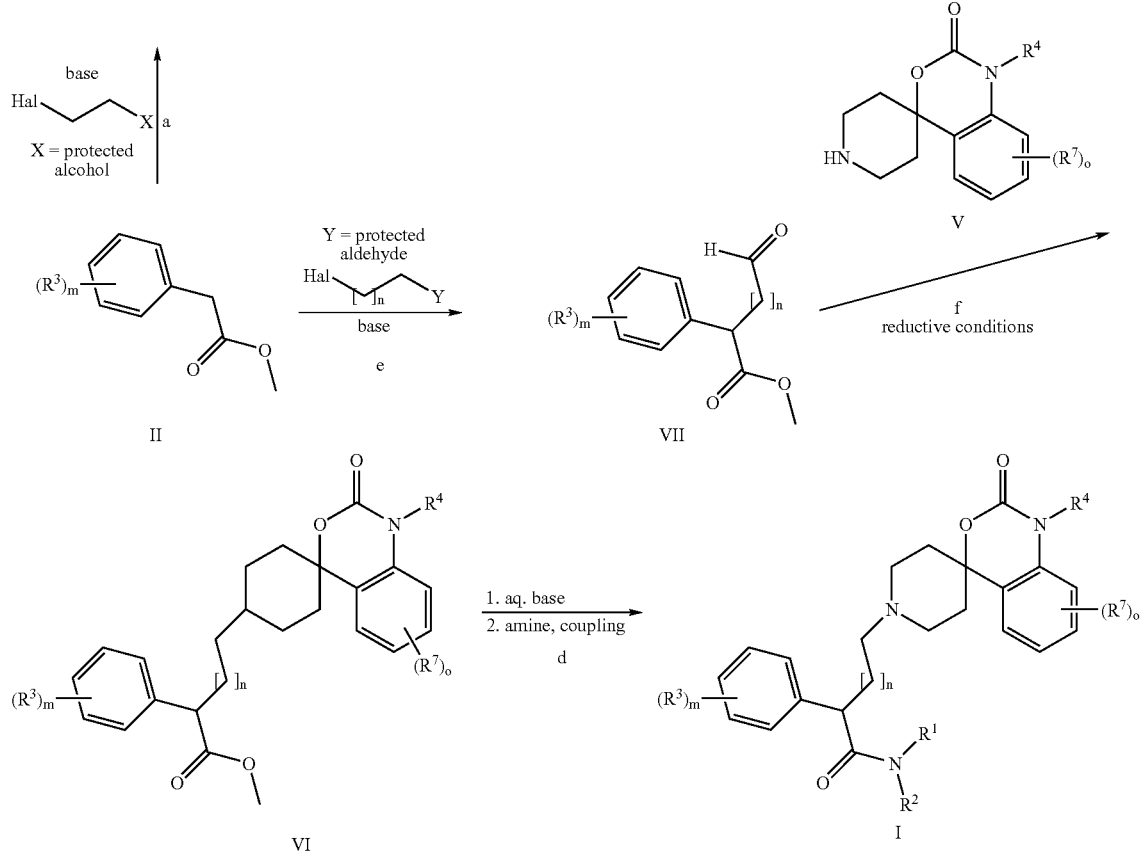

In the above scheme 1, $R^1$, $R^2$, $R^3$, $R^4$, n and m have same meanings as described before.

a) Phenylacetic acid ester derivatives II are commercially available or can be accessed by methods described in literature. Reaction of ester derivatives II with hydroxy-protected alkyl halides (either commercially available or synthetically accessible by methods known in the art) under basic conditions lead upon cleavage of the hydroxyl protecting group to lactones III as described in literature (for reaction conditions described in literature affecting such reactions see for example: *Comprehensive Organic Transformations: A Guide to Functional Group Preparations, 2nd Edition*, Richard C. Larock. John Wiley & Sons, New York, N.Y. 1999). However, it is convenient to react ester derivative II with 2-(2-bromoethoxy)tetrahydro-2-H-pyrane (commercially available in the presence of a base and a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction may equally be employed here. Examples of such bases include NaH and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the hydroxy protected intermediate which can be subjected to acidic cleavage of the protecting group in the presence of a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the acid used in this stage, and any acid commonly used in this type of reaction may equally be employed here. Examples of such acid include HCl and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield lactone derivatives III.

b) Lactone derivative III can conveniently transferred into the respective ester derivative IV by a two step reaction sequence. Any commonly used synthetic sequence is applicable, however, we find it convenient to open the lactone derivative III with HBr in the presence of an acid. Any commonly used acid which in combination with HBr affects such a reaction can be used. Examples of such acids include acetic acid and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediately built acid derivative which is subjected to esterification conditions. Common procedures are described in literature, however, we find it convenient to transform the intermediately built acid into the respective ester derivative IV by reaction with SOCl$_2$ in methanol. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield ester derivative IV.

c) Transformation of ester derivative IV with spiropiperidine derivatives V (synthetic access described in literature: see for instance *Journal of Medicinal Chemistry* (1983), 26(5), 657-61) to access spiropiperidine derivatives VI can be affected by any commonly used procedure. However, we find it convenient to react ester derivative IV with spiropiperidine derivatives V in the presence of a solvent and a base. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction may equally be employed here. Examples of such bases include DIPEA, NEt$_3$ and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield spiropiperidine derivative VI.

d) Transformation of spiropiperidine derivative VI into the final amide derivatives I can be done according to procedures described in literature. However, we find it convenient to employ a two step reaction sequence in which the ester functionality in VI is cleaved under aqueous basic conditions and the liberated acid functionality VIII or a salt thereof

VIII

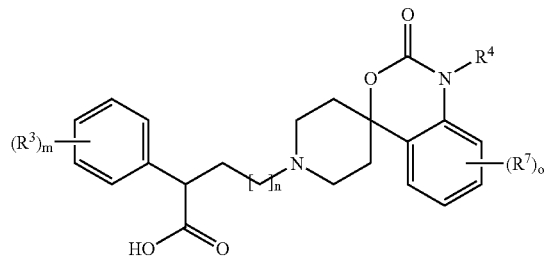

[R$^3$, R$^4$, n, o and m have same meanings as described before]

converted with the respective amines IX

IX

wherein R$^1$ and R$^2$ have same meanings as described before, under coupling conditions to produce the spiropiperidine derivatives I. There is no particular restriction on the nature of the aqueous base to be employed, provided that it has no adverse effect on the reaction or the reagents involved and that it can dissolve the reagents, at least to some extent. Examples for suitable aqueous bases include NaOH, LiOH and the like. Any commonly used co-solvent can be employed. Examples include THF and the like. The coupling of carboxylic acids with amines is widely described in literature and the procedures are known to those in the art (For reaction conditions described in literature affecting such reactions see for example: *Comprehensive Organic Transformations: A Guide to Functional Group Preparations*, 2nd Edition, Richard C. Larock. John Wiley & Sons, New York, N.Y. 1999). The intermediately built acid VIII can conveniently be transformed to the respective amide I through coupling with an amine IX (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield spiropiperidine derivatives I.

e) Reaction of ester derivatives II with protected bromo alkyl aldehydes (either commercially available or synthetically accessible by methods known in the art) under basic conditions lead to aldehyde derivatives VII as described analogously in literature (for reaction conditions described in literature affecting such reactions see for example: *Comprehensive Organic Transformations: A Guide to Functional Group Preparations*, 2nd Edition, Richard C. Larock.

John Wiley & Sons, New York, N.Y. 1999). However, it is convenient to react ester derivative II with the respective protected bromo alkyl aldehyde (commercially available or accessible by methods known) in the presence of a base and a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction may equally be employed here. Examples of such bases include NaH and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the aldehyde protected intermediate which can be subjected to acidic cleavage of the protecting group in the presence of a solvent. There is no particular restriction on the nature of the solvent to be employed, provided that it has no adverse effect on the reaction or the reagents involved and that it can dissolve the reagents, at least to some extent. Examples for suitable solvents include tetrahydrofuran (THF) and the like. There is no particular restriction on the nature of the acid used in this stage, and any acid commonly used in this type of reaction may equally be employed here. Examples of such acid include HCl and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield aldehyde derivatives VII.

f) Reductive animations are widely described in literature (for reaction conditions described in literature affecting such reactions see for example: *Comprehensive Organic Transformations: A Guide to Functional Group Preparations, 2nd Edition*, Richard C. Larock. John Wiley & Sons, New York, N.Y. 1999). However, we find it convenient to transform aldehyde derivative VII with spiropiperidine derivatives V (*Journal of Medicinal Chemistry* (1983), 26(5), 657-61) under reductive conditions in the presence of a solvent to afford ester derivatives VI. There is no particular restriction on the nature of the solvent to be employed, provided that it has no adverse effect on the reaction or the reagents involved and that it can dissolve the reagents, at least to some extent. Examples for suitable solvents include tetrahydrofuran (THF) and the like. There is no particular restriction on the nature of the reducing agent used in this stage, and any reducing agent commonly used in this type of reaction may equally be employed here. Examples of such reducing agents include sodium triacetoxyborohydride and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield ester derivative VI.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methane-sulphonates, p-toluenesulphonates and the like are examples of such salts.

As mentioned earlier, the compounds of formula I and their pharmaceutically usable addition salts possess valuable pharmacological properties. Compounds of the present invention are allosteric positive modulators of neurokinin 3 (NK-3) receptors. The compounds were investigated in accordance with the tests given hereinafter.

Experimental Procedure

The compounds were investigated in accordance with the tests given hereinafter.

[$^3$H]SR142801 Competition Binding Assay hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM $MnCl_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S.A., Zürich, Switzerland) and shaking for 1 h. Inhibition curves were fitted according to the Hill equation: $y=100/(1+(x/IC_{50})^{n_H})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean±standard error (SEM) of the individual $K_i$ values was calculated.

Results of some representative compounds with a good hNK-3 receptor affinity are shown in Table 1.

TABLE 1

| Example | Compound name | hNK₃ Ki [μM] |
|---|---|---|
| 1 | N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride | 0.0112 |
| 6 | N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide | 0.0628 |
| 8 | N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide | 0.017 |
| 9 | 2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide | 0.0914 |
| 12 | 2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide | 0.0312 |
| 14 | N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.0908 |
| 15 | N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.0037 |
| 17 | N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.0067 |
| 18 | 2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide | 0.0157 |
| 19 | N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.0052 |
| 25 | N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 0.0594 |
| 26 | N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 0.0383 |
| 27 | N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 0.0385 |
| 29 | N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide | 0.0067 |
| 31 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide | 0.0058 |
| 32 | N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 0.0039 |
| 33 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide | 0.0547 |
| 34 | N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 0.0033 |
| 38 | 1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one | 0.0487 |
| 39 | 2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide | 0.0042 |
| 40 | N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.0011 |
| 42 | N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.0008 |
| 43 | 1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one | 0.0619 |
| 44 | N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.0016 |
| 47 | N-(2,4-dichlorobenzyl)-4-(6-fluoro-2-oxo-1,2-dihydro-1'H-spiro[3,1-benzoxazine-4,4'-piperidin]-1'-yl)-2-(4-fluorophenyl)butanamide | 0.0827 |
| 49 | 4-(6-fluoro-2-oxo-1,2-dihydro-1'H-spiro[3,1-benzoxazine-4,4'-piperidin]-1'-yl)-2-(4-fluorophenyl)-N-[2-(trifluoromethoxy)benzyl]butanamide | 0.0909 |
| 51 | 4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide | 0.0322 |
| 56 | 4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide | 0.0664 |
| 58 | 4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide | 0.0949 |
| 59 | N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 0.0489 |
| 61 | 4-(6-fluoro-2-oxo-1,2-dihydro-1'H-spiro[3,1-benzoxazine-4,4'-piperidin]-1'-yl)-2-(4-fluorophenyl)-N-[3-(trifluoromethyl)benzyl]butanamide | 0.0885 |
| 62 | N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide | 0.01 |
| 64 | N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.0125 |
| 65 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide | 0.0707 |
| 66 | 2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide | 0.0288 |
| 67 | 2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide | 0.019 |
| 68 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide | 0.0014 |
| 70 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide | 0.098 |
| 72 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide | 0.0187 |
| 74 | 2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide | 0.0055 |
| 75 | 2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide | 0.0077 |
| 76 | 2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide | 0.0046 |
| 77 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide | 0.0046 |
| 78 | 2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide | 0.0154 |
| 79 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide | 0.0066 |
| 80 | 2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide | 0.0044 |

TABLE 1-continued

| Example | Compound name | hNK₃ Ki [μM] |
|---|---|---|
| 81 | 2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide | 0.0116 |
| 82 | 2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide | 0.0197 |
| 83 | 2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide | 0.0129 |
| 84 | 2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide | 0.0116 |
| 85 | 2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide | 0.0699 |
| 86 | N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide | 0.0121 |
| 87 | N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 0.0021 |
| 88 | N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 0.0722 |
| 89 | N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.0008 |
| 90 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide | 0.008 |
| 91 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide | 0.0065 |
| 92 | 2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide | 0.0028 |
| 93 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide | 0.0006 |
| 94 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide | 0.0877 |
| 95 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide | 0.0288 |
| 97 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide | 0.0094 |
| 99 | 2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide | 0.0024 |
| 100 | 2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide | 0.0026 |
| 101 | 2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide | 0.0013 |
| 102 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide | 0.0021 |
| 103 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide | 0.0037 |
| 104 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide | 0.0016 |
| 105 | 2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide | 0.001 |
| 106 | 2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide | 0.0027 |
| 107 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide | 0.0054 |
| 108 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide | 0.003 |
| 109 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide | 0.019 |
| 110 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide | 0.0032 |
| 111 | N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 0.0031 |
| 116 | 2-(3,4-dichlorophenyl)-5-(6-fluoro-2-oxo-1,2-dihydro-1'H-spiro[3,1-benzoxazine-4,4'-piperidin]-1'-yl)-N-[(3-methyl-2-thienyl)methyl]pentanamide | 0.0668 |
| 118 | 2-(3,4-dichlorophenyl)-5-(6-fluoro-2-oxo-1,2-dihydro-1'H-spiro[3,1-benzoxazine-4,4'-piperidin]-1'-yl)-N-[2-(trifluoromethoxy)benzyl]pentanamide | 0.0644 |
| 120 | N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide | 0.0463 |
| 121 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide | 0.0647 |
| 125 | N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)pentanamide | 0.0983 |
| 130 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide | 0.0919 |
| 131 | 2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide | 0.0692 |
| 132 | 2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)pentanamide | 0.0657 |
| 135 | 2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethyl)benzyl]pentanamide | 0.0903 |
| 138 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide | 0.0954 |
| 146 | (2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride | 0.0057 |
| 147 | (2R)—N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.0018 |

TABLE 1-continued

| Example | Compound name | hNK$_3$ Ki [μM] |
|---|---|---|
| 148 | (2S)—N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.0004 |

Furthermore, as indicated above, compounds of the present invention have also good activities toward the NK-1 and NK-2 receptors.

Some examples of such activity are given in Table 2:

TABLE 2

| Example | Compound name | hNK1 μM | hNK2 μM |
|---|---|---|---|
| 1 | N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride | 0.171 | 0.009 |
| 17 | N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.111 | 0.0053 |
| 19 | N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 0.066 | 0.0081 |
| 40 | N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.035 | 0.0052 |
| 42 | N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.116 | 0.012 |
| 44 | N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 0.118 | 0.0028 |

The present invention also provides pharmaceutical compositions containing compounds of the invention, for example compounds of formula I, or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

EXAMPLE A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

EXAMPLE C

Suppositories of the following composition can be manufactured:

|  | mg/supp. |
|---|---|
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size, left to cool, the suppositories then can be removed from the moulds and packed individually in wax paper or metal foil.

The following Examples illustrate the present invention without limiting it. All temperatures are given in degrees Celsius.

Abbreviations

DCM=dichloromethane;
DIPEA=N,N-diisopropylethylamine;
DMF=N,N-dimethylformamide;
HPLC=high-performance liquid chromatography;
MS=mass spectroscopy;
THF=tetrahydrofurane.

Intermediate 1

6-Fluorospiro[3,1-benzoxazine-4,4'-piperidin]-2(1H)-one; hydrochloride

A mixture of 48.96 g (232 mmol) (4-fluoro-phenyl)-carbamic acid tert-butyl ester and 300 mL tert-BuLi (1.7 M in hexane) in 380 mL THF at −70° C. was stirred for 50 min and afterwards 2.5 h at −20° C. 44.3 g (223 mmol) 4-oxo-piperidine-1-carboxylic acid tert-butyl ester (commercially available) in 180 mL THF was added at −70° C. and 60 mg KOtBu at 15° C. The mixture was stirred at room temperature for 14 h. NH₄Cl aq. was added, the organic phase was washed with saturated NaCl aq., and the aqueous phase was extracted with a mixture of THF and ethyl acetate. The combined organic phases were dried with Na₂SO₄ and evaporated to dryness. The residue was titurated with diethyl ether, filtered off, washed with diethyl ether and dried to yield 31 g of tert-butyl 6-fluoro-2-oxo-1,2-dihydro-1'H-spiro[3,1-benzoxazine-4,4'-piperidine]-1'-carboxylate (MS (m/e): 335.5 (MH⁻)) which was used without further purification in the consecutive step. 300 mL dioxane and 136 mL 4N HCl in dioxane was added and stirred at room temperature for 18 h. The precipitate was filtered off, washed with dioxane and diethyl ether and dried in vacuum. 21 g (36%) of the title compound was yielded as light yellow solid. MS (m/e): 237.1 (MH⁺).

Intermediate 2

6-Fluoro-1-methylspiro[3,1-benzoxazine-4,4'-piperidin]-2(1H)-one; hydrochloride

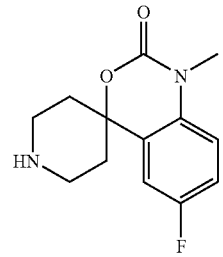

A mixture of 3.67 g (11 mmol) tert-butyl 6-fluoro-2-oxo 1,2-dihydro-1'H-spiro[3,1-benzoxazine-4,4'-piperidine]-1'-carboxylate, 3.09 g (21.8 mmol) methyl iodide (commercially available) and 5.33 g (16 mmol) Cs₂CO₃ in 30 mL DMF was stirred at room temperature for 17 h. The mixture was poured onto ice/water and extracted with ethyl acetate. The combined organic phases were dried with Na₂SO₄ and evaporated to dryness. 40 mL dioxane and 15 mL 4 N HCl in dioxane was added and the mixture was stirred at room temperature for 3 h. The precipitate was filtered off, washed with diethyl ether and dried in vacuum to yield 2.5 g (80%) of the title compound as off-white solid. MS (m/e): 251.3 (MH⁺).

EXAMPLE 1

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride

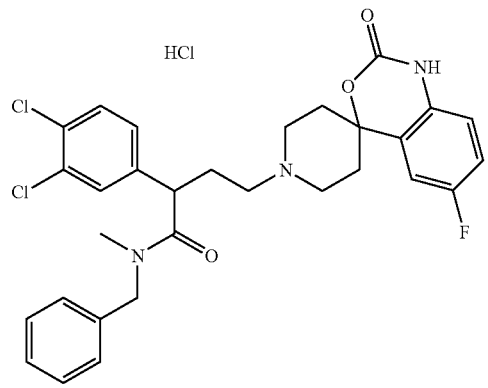

a) Step 1

3-(3,4-Dichloro-phenyl)-dihydro-furan-2-one

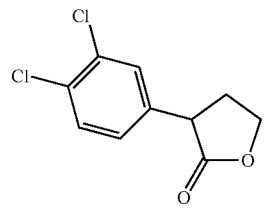

A mixture of 30 g (137 mmol) (3,4-Dichloro-phenyl)-acetic acid methyl ester (commercially available), 6.47 g (151 mmol) NaH (55%) and 35.8 g (171 mmol) 2-(2-Bromo-ethoxy)-tetrahydro-pyran in 100 mL DMF was stirred at room temperature for 17 h. The mixture was evaporated to dryness and partitioned between water and ethyl acetate. The combined organic phases were washed with NaCl aq., dried with Na₂SO₄ and evaporated. The residue was treated with 400 mL 4N HCl in dioxane in 250 mL methanol and stirred for 16 h at room temperature. The mixture was evaporated to dryness and subjected to column chromatography on silica eluting with a gradient formed from ethyl acetate and heptane. The combined product fractions were evaporated to yield 18.5 g (58%) of the title compound as yellow oil.

b) Step 2

4-Bromo-2-(3,4-dichloro-phenyl)-butyric acid methyl ester

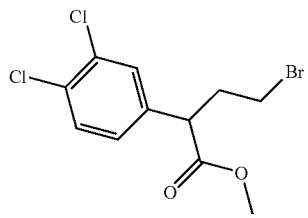

A mixture of 10.2 g (44 mmol) 3-(3,4-dichloro-phenyl)-dihydro-furan-2-one, 55 mL HBr in acetic acid (33%) in 20 mL acetic acid was stirred at room temperature for 16 h. The mixture was poured onto ice/water and extracted with isopropylethyl acetate. The combined organic phases were washed with NaCl aq., dried with Na₂SO₄ and evaporated. 26.3 g (221 mmol) SOCl₂ and 200 mL toluene was added and heated to 80° C. for 3 h. The mixture was evaporated to dryness and 100 mL methanol was added and stirred at room temperature for 30 min. The mixture was evaporated and subjected to column chromatography on silica eluting with a gradient formed from ethyl acetate and heptane. The combined product fractions were evaporated to yield 12.7 g (88%) of the title compound as light brown oil. MS (m/e): 335.5 (MH⁻).

c) Step 3

Methyl 2-(3,4-dichlorophenyl)-4-(6-fluoro-2-oxo-1,2-dihydro-1'H-spiro[3,1-benzoxazine-4,4'-piperidin]-1'-yl)butanoate

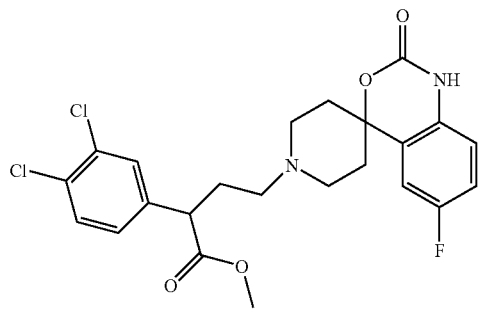

A mixture of 1.5 g (4.6 mmol) 4-bromo-2-(3,4-dichlorophenyl)-butyric acid methyl ester, 1.38 g (5 mmol) 6-fluorospiro[3,1-benzoxazine-4,4'-piperidin]-2(1H)-one; hydrochloride (intermediate 1) and 1.3 g (10 mmol) DIPEA in 30 mL DMF was stirred at room temperature for 16 h. The mixture was evaporated and subjected to column chromatography on silica eluting with a gradient formed from DCM, methanol and NEt₃. The product containing fractions were evaporated to yield 0.4 g (18%) of the title compound as light yellow foam. MS (m/e): 481.1 (MH⁺).

d) Step 4

Intermediate 3

2-(3,4-dichlorophenyl)-4-(6-fluoro-2-oxo-1,2-dihydro-1'H-spiro[3,1-benzoxazine-4,4'-piperidin]-1'-yl)butanoic acid; hydrochloride

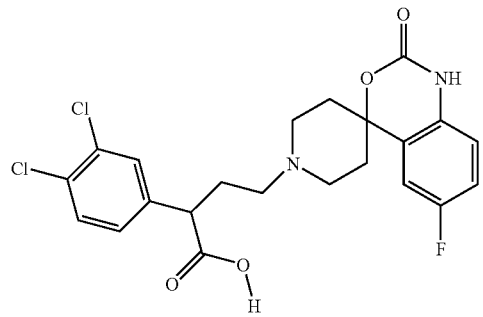

A mixture of 0.38 g (0.79 mmol) methyl 2-(3,4-dichlorophenyl)-4-(6-fluoro-2-oxo-1,2-dihydro-1'H-spiro[3,1-benzoxazine-4,4'-piperidin]-1'-yl)butanoate, 0.166 g (3.96 mmol) LiOH.H₂O in 15 mL THF and 15 mL water was heated to reflux for 2 h. The mixture was concentrated and acidified with 4N HCl aq. The precipitate was filtered off, dried under vacuum and used in the consecutive step without further purification. MS (m/e): 467.1 (MH⁺).

e) Step 5

A mixture of 2-(3,4-dichlorophenyl)-4-(6-fluoro-2-oxo-1,2-dihydro-1'H-spiro[3,1-benzoxazine-4,4'-piperidin]-1'-yl) butanoic acid; hydrochloride, 0.38 g (1.18 mmol) TBTU, 0.61 g (4.7 mmol) DIPEA and 0.12 g (1 mmol) N-methylbenzylamine in 30 mL DMF was stirred at room temperature for 16 h. The mixture was evaporated and subjected to column chromatography on silica eluting with a gradient formed from DCM, methanol and NEt₃. The product containing fractions were evaporated, dissolved in methanol and treated with HCl in methanol. The mixture was evaporated, dissolved in methanol, charcoal was added, filtered and again evaporated and dried to yield 0.19 g (39%) of the title compound as light brown foam. MS (m/e): 570.3 (MH⁺).

EXAMPLE 2

N-benzyl-2-(3,4-dichlorophenyl)-4-(6-fluoro-2-oxo-1,2-dihydro-1'H-spiro[3,1-benzoxazine-4,4'-piperidin]-1'-yl)butanamide

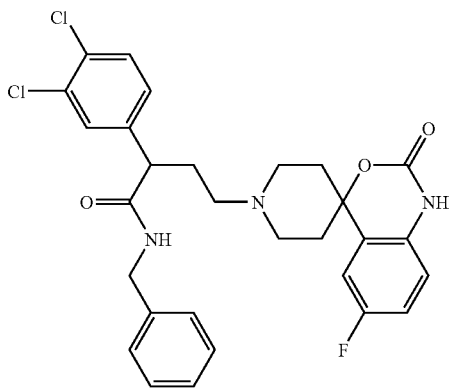

a) Step 1

2-(3,4-Dichloro-phenyl)-4-oxo-butyric acid methyl ester

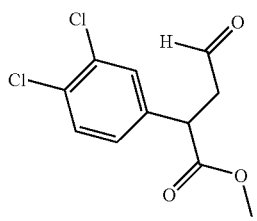

A mixture of 25 g (114 mmol) (3,4-dichloro-phenyl)-acetic acid methyl ester (commercially available), 5.7 g (131 mmol) NaH (55%) and 23.1 g (137 mmol) bromoacetaldehyde dimethylacetal in 80 mL DMF was stirred at room temperature for 3 h. The mixture was poured onto ice/water and extracted with ethyl acetate. The combined organic phases were washed with NaCl aq., dried with $Na_2SO_4$ and evaporated to dryness. The residue was dissolved in 250 mL THF and treated with 300 mL 1 N HCl at room temperature for 20 h. Water was added and the mixture was extracted with ethyl acetate. The combined organic phases were washed with NaCl aq., dried with $Na_2SO_4$, evaporated to dryness and subjected to column chromatography on silica eluting with a gradient formed from heptane and ethyl acetate. The product containing fractions were evaporated to yield 9.7 g (32%) of the title compound as light yellow oil. MS (m/e): 260.1/262.2 (MH$^+$).

b) Step 2

Methyl 2-(3,4-dichlorophenyl)-4-(6-fluoro-2-oxo-1,2-dihydro-1'H-spiro[3,1-benzoxazine-4,4'-piperidin]-1'-yl)butanoate

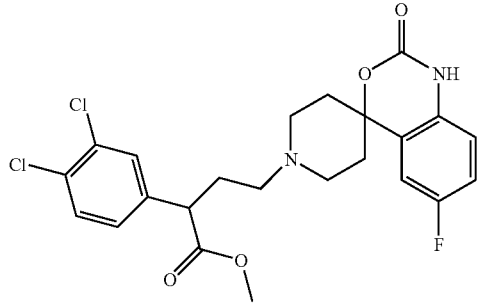

A mixture of 6.45 g (24.7 mmol) 2-(3,4-dichloro-phenyl)-4-oxo-butyric acid methyl ester, 6.42 g (27 mmol) 6-fluorospiro[3,1-benzoxazine-4,4'-piperidin]-2(1H)-one, 7.85 g (47 mmol) sodium triacetoxyborohydride and 2.22 g acetic acid in 200 mL THF was stirred at room temperature for 16 h. $Na_2CO_3$ aq and water was added and the mixture was extracted with ethyl acetate. The combined organic phases were washed with NaCl aq., dried with $Na_2SO_4$ and evaporated to dryness. The residue was subjected to column chromatography on silica eluting with a gradient formed from DCM, methanol and NEt$_3$. The product containing fractions were evaporated to yield 10.2 g (86%) of the title compound as off-white yellow foam. MS (m/e): 481.1 (MH$^+$).

c) Step 3

2-(3,4-dichlorophenyl)-4-(6-fluoro-2-oxo-1,2-dihydro-1'H-spiro[3,1-benzoxazine-4,4'-piperidin]-1'-yl) butanoic acid, hydrochloride

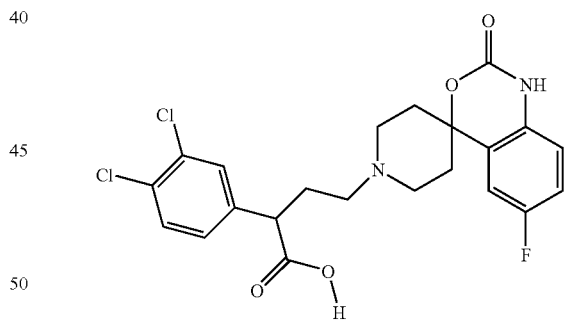

In analogy to the procedure described for example 1, step 4, the title compound was prepared from methyl 2-(3,4-dichlorophenyl)-4-(6-fluoro-2-oxo-1,2-dihydro-1'H-spiro[3,1-benzoxazine-4,4'-piperidin]-1'-yl)butanoate through saponification with LiOH.H$_2$O and hydrochloride formation with HCl aq. MS (m/e): 467.1 (MH$^+$).

d) Step 4

In analogy to the coupling procedure described for example 1, step 5, the title compound was prepared from 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride and benzylamine (commercially available) and subsequent subjection to purification by preparative HPLC on reversed phase eluting with a gradient formed from acetonitrile, water and NEt₃. The combined product fractions were evaporated to yield the title compound as off-white solid. MS (m/e): 556.1 (MH⁺).

Intermediate 4

2-(4-fluorophenyl)-4-(6-fluoro-2-oxo-1,2-dihydro-1'H-spiro[3,1-benzoxazine-4,4'-piperidin]-1'-yl)butanoic acid, hydrochloride

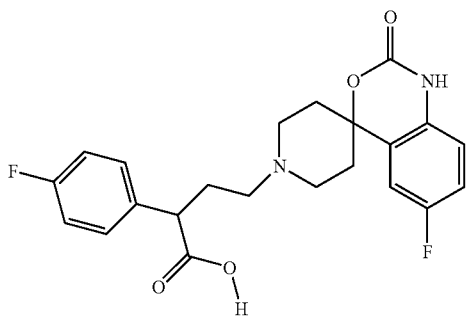

a) Step 1

2-(4-Fluoro-phenyl)-4-oxo-butyric acid methyl ester

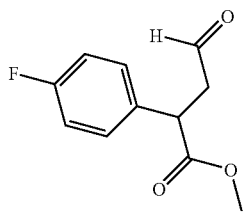

In analogy to the procedure described for the synthesis of 2-(3,4-Dichloro-phenyl)-4-oxo-butyric acid methyl ester (example 2, step 1) the title compounds was prepared from 4-fluoro-phenyl-acetic acid methyl ester (commercially available), and bromoacetaldehyde dimethylacetal and subsequent treatment with HCl aq. MS (m/e): 209.3 (MH⁻).

b) Step 2

Methyl 2-(4-fluorophenyl)-4-(6-fluoro-2-oxo-1,2-dihydro-1'H-spiro[3,1-benzoxazine-4,4'-piperidin]-1'-yl)butanoate

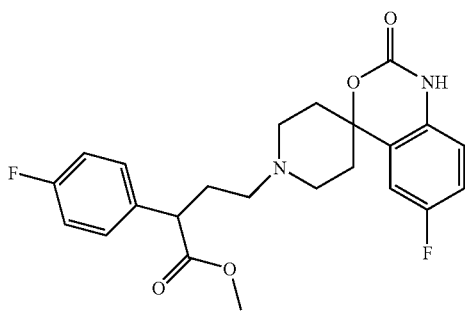

In analogy to the procedure described for the synthesis of methyl 2-(3,4-dichlorophenyl)-4-(6-fluoro-2-oxo-1,2-dihydro-1'H-spiro[3,1-benzoxazine-4,4'-piperidin]-1'-yl)butanoate (example 2, step 2) the title compound was prepared from 2-(4-fluoro-phenyl)-4-oxo-butyric acid methyl ester and 6-fluorospiro[3,1-benzoxazine-4,4'-piperidin]-2(1H)-one; hydrochloride (intermediate 1). MS (m/e): 431.3 (MH⁺).

c) Step 3

In analogy to the procedure described for example 1, step 4, the title compound was prepared from methyl 2-(4-fluorophenyl)-4-(6-fluoro-2-oxo-1,2-dihydro-1'H-spiro[3,1-benzoxazine-4,4'-piperidin]-1'-yl)butanoate through saponification with LiOH.H₂O and hydrochloride formation with HCl aq. MS (m/e): 417.4 (MH⁺).

Intermediate 5

2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride

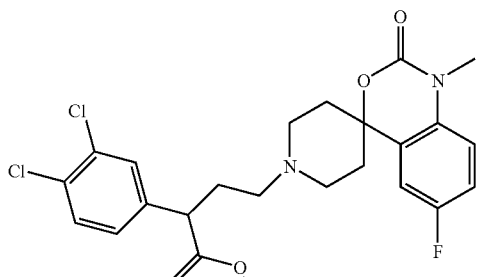

a) Step 1

Methyl 2-(3,4-dichlorophenyl)-4-(1-methyl-2-oxo-1,2-dihydro-1'H-spiro[3,1-benzoxazine-4,4'-piperidin]-1'-yl)butanoate

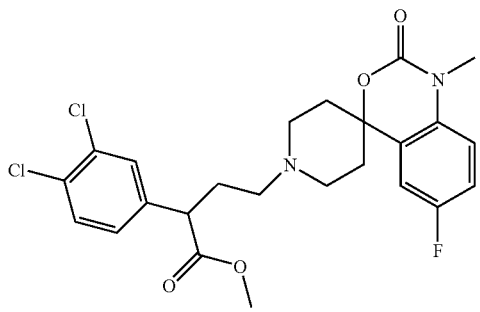

In analogy to the procedure described for the synthesis of methyl 2-(3,4-dichlorophenyl)-4-(6-fluoro-2-oxo-1,2-dihydro-1'H-spiro[3,1-benzoxazine-4,4'-piperidin]-1'-yl)butanoate (example 2, step 2) the title compound was prepared from 2-(3,4-dichloro-phenyl)-4-oxo-butyric acid methyl ester and 6-fluoro-1-methylspiro[3,1-benzoxazine-4,4'-piperidin]-2(1H)-one; hydrochloride (intermediate 2). MS (m/e): 495.4 (MH⁺).

b) Step 2

In analogy to the procedure described for example 1, step 4, the title compound was prepared from methyl 2-(3,4-dichlorophenyl)-4-(1-methyl-2-oxo-1,2-dihydro-1'H-spiro[3,1-benzoxazine-4,4'-piperidin]-1'-yl)butanoate through saponification with LiOH.H₂O and hydrochloride formation with HCl aq. MS (m/e): 481.1 (MH⁺).

a) Step 1

2-(3,4-Dichloro-phenyl)-5-oxo-pentanoic acid methyl ester

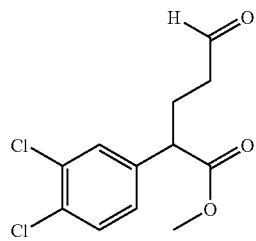

In analogy to the procedure described for the synthesis of 2-(3,4-dichloro-phenyl)-4-oxo-butyric acid methyl ester (example 2, step 1) the title compounds was prepared from 3,4-dichloro-phenyl-acetic acid methyl ester (commercially available), and 3-bromopropionaldehyde dimethylacetal and subsequent treatment with HCl aq. MS (m/e): 274.1/276.1 (MH$^+$).

b) Step 2

Methyl 2-(3,4-dichlorophenyl)-5-(6-fluoro-2-oxo-1,2-dihydro-1'H-spiro[3,1-benzoxazine-4,4'-piperidin]-1'-yl)pentanoate

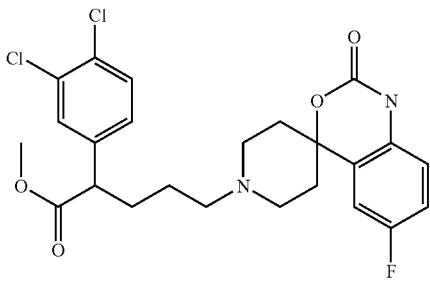

In analogy to the procedure described for the synthesis of methyl 2-(3,4-dichlorophenyl)-4-(6-fluoro-2-oxo-1,2-dihydro-1'H-spiro[3,1-benzoxazine-4,4'-piperidin]-1'-yl)butanoate (example 2, step 2) the title compound was prepared from 2-(3,4-dichloro-phenyl)-5-oxo-pentanoic acid methyl ester and 6-fluorospiro[3,1-benzoxazine-4,4'-piperidin]-2(1H)-one; hydrochloride (intermediate 1). MS (m/e): 495.4 (MH$^+$).

c) Step 3

In analogy to the procedure described for example 1, step 4, the title compound was prepared from methyl 2-(3,4-dichlorophenyl)-5-(6-fluoro-2-oxo-1,2-dihydro-1'H-spiro[3,1-benzoxazine-4,4'-piperidin]-1'-yl)pentanoate through saponification with LiOH.H$_2$O and hydrochloride formation with HCl aq. MS (m/e): 481.1 (MH$^+$).

In analogy to the synthesis of example 2 further 6-fluoro-2-oxo-1,2-dihydro-1'H-spiro[3,1-benzoxazine-4,4'-piperidin derivatives have been prepared from their respective starting materials mentioned in table 2. Table 2 comprises example 3 to example 148. Optionally final compounds can be purified by column chromatography on silica eluting with appropriate solvent mixtures. Optionally final compounds can be transferred into their respective salts by treatment with appropriate acids. Diastereomeric or racemic mixtures can be separated into their respective diastereoisomer or enantiomer by chromatographic techniques as appropriate.

TABLE 2

| Exp | MW | Structure | Compound name | Starting materials | MW found MH+ |
|---|---|---|---|---|---|
| 3 | 557.45 | 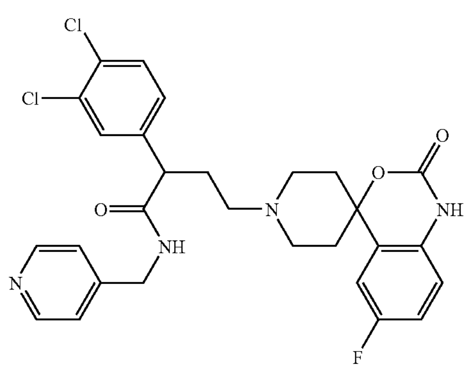 | 2-(3,4-dichlorophenyl)-4-(6-fluoro-2-oxo-1,2-dihydro-1'H-spiro[3,1-benzoxazine-4,4'-piperidin]-1'-yl)-N-(pyridin-4-ylmethyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and C-Pyridin-4-yl-methylamine (commercially available) | 557.2 |

TABLE 2-continued

| Exp | MW | Structure | Compound name | Starting materials | MW found MH+ |
|---|---|---|---|---|---|
| 4 | 582.5 | 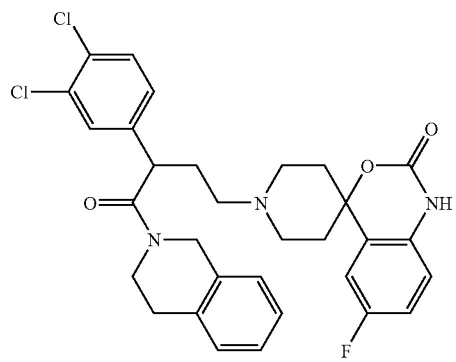 | 1'-[3-(3,4-dichlorophenyl)-4-(3,4-dihydroisoquinolin-2(1H)-yl)-4-oxobutyl]-6-fluorospiro[3,1-benzoxazine-4,4'-piperidin]-2(1H)-one | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 1,2,3,4-Tetrahydro-isoquinoline (commercially available) | 582.3 |
| 5 | 505.56 | 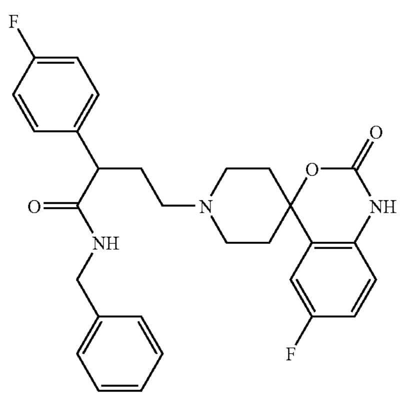 | N-benzyl-4-(6-fluoro-2-oxo-1,2-dihydro-1'H-spiro[3,1-benzoxazine-4,4'-piperidin]-1'-yl)-2-(4-fluorophenyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Benzylamine (commercially available) | 506.1 |
| 6 | 584.52 | 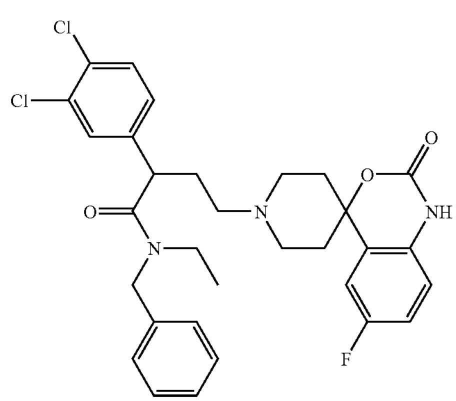 | N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Benzyl-ethyl-amine (commercially available) | 586.1 |

TABLE 2-continued

| Exp | MW | Structure | Compound name | Starting materials | MW found MH+ |
|---|---|---|---|---|---|
| 7 | 634.55 | 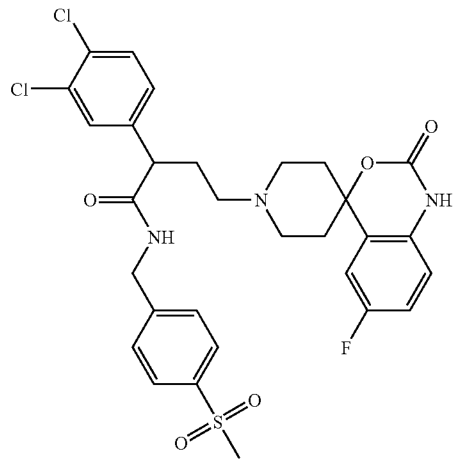 | 2-(3,4-dichlorophenyl)-4-(6-fluoro-2-oxo-1,2-dihydro-1'H-spiro[3,1-benzoxazine-4,4'-piperidin]-1'-yl)-N-[4-(methylsulfonyl)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Methanesulfonyl-benzylamine (commercially available) | 634.3 |
| 8 | 590.91 | 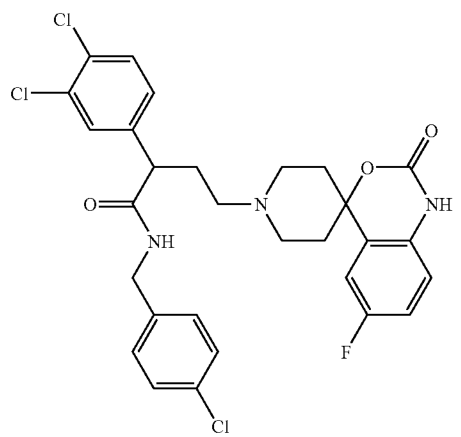 | N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Chloro-benzylamine (commercially available) | 590.3 |
| 9 | 560.45 | 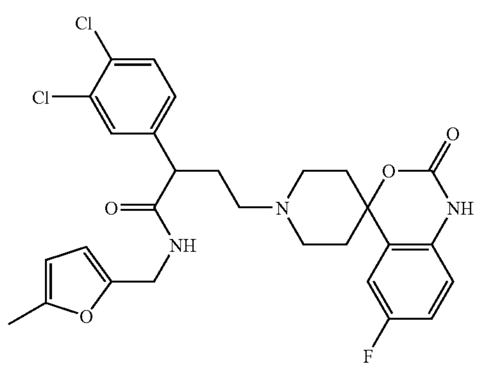 | 2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and C-(5-Methyl-furan-2-yl)methylamine (commercially available) | 560.3 |

TABLE 2-continued

| Exp | MW | Structure | Compound name | Starting materials | MW found MH+ |
|---|---|---|---|---|---|
| 10 | 576.52 | 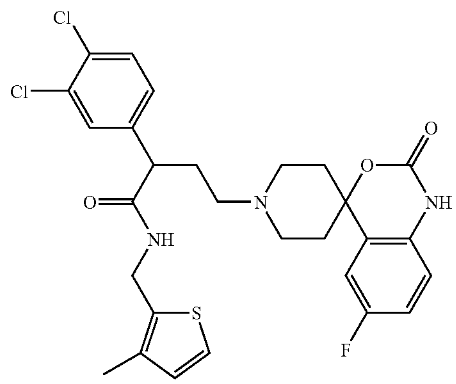 | 2-(3,4-dichlorophenyl)-4-(6-fluoro-2-oxo-1,2-dihydro-1'H-spiro[3,1-benzoxazine-4,4'-piperidin]-1'-yl)-N-[(3-methyl-2-thienyl)methyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and C-(3-Methyl-thiophen-2-yl)-methylamine (commercially available) | 576.3 |
| 11 | 585.51 | 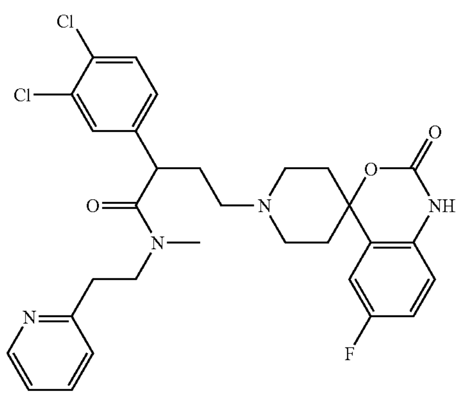 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-pyridin-2-ylethyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 2-Pyridin-2-yl-ethylamine (commercially available) | 585.2 |
| 12 | 602.51 | 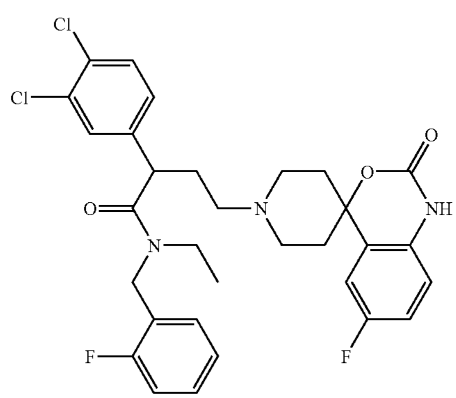 | 2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Ethyl-(2-fluoro-benzyl)-amine (commercially available) | 602.5 |

TABLE 2-continued

| Exp | MW | Structure | Compound name | Starting materials | MW found MH+ |
|---|---|---|---|---|---|
| 13 | 644.57 | 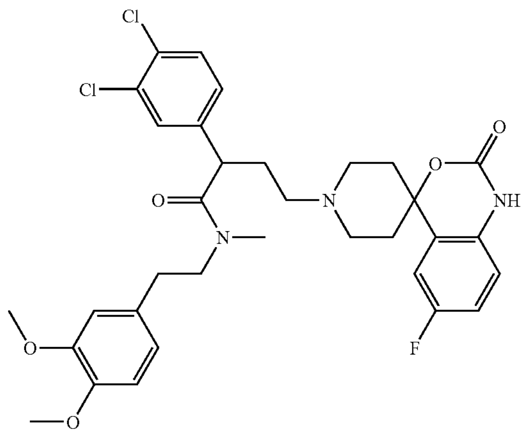 | 2-(3,4-dichlorophenyl)-N-[2-(3,4-dimethoxyphenyl)ethyl]-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and [2-(3,4-Dimethoxy-phenyl)-ethyl]-methyl-amine (commercially available) | 644.5 |
| 14 | 536.47 | 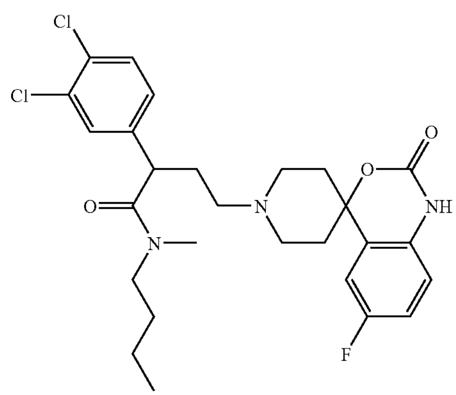 | N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Butyl-methyl-amine (commercially available) | 536.3 |
| 15 | 604.94 | 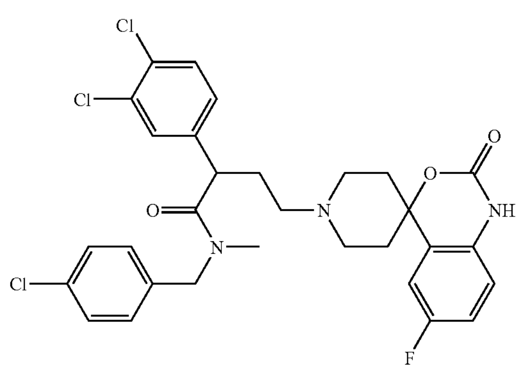 | N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Chloro-benzylamine (commercially available) | 606.3 |

TABLE 2-continued

| Exp | MW | Structure | Compound name | Starting materials | MW found MH+ |
|---|---|---|---|---|---|
| 16 | 624.58 | 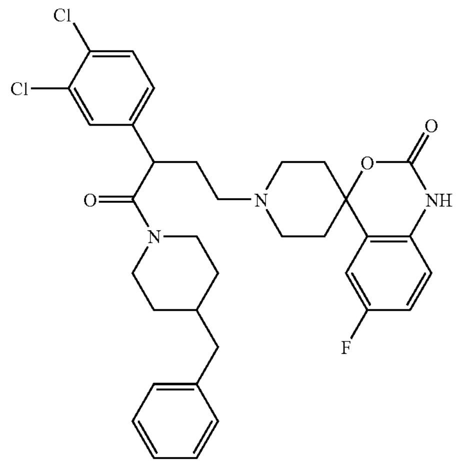 | 1'-[4-(4-benzylpiperidin-1-yl)-3-(3,4-dichlorophenyl)-4-oxobutyl]-6-fluorospiro[3,1-benzoxazine-4,4'-piperidin]-2(1H)-one | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Benzyl-piperidine (commercially available) | 624.3 |
| 17 | 604.94 | 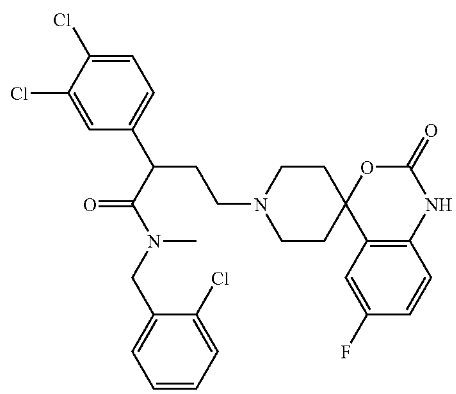 | N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (2-Chloro-benzyl)-methyl-amine (commercially available) | 606.3 |
| 18 | 598.55 | 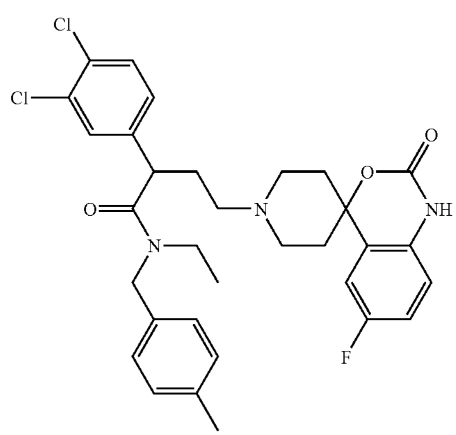 | 2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butnamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Ethyl-(4-methyl-benzyl)-amine (commercially available) | 598.3 |

TABLE 2-continued

| Exp | MW | Structure | Compound name | Starting materials | MW found MH+ |
|---|---|---|---|---|---|
| 19 | 604.94 | 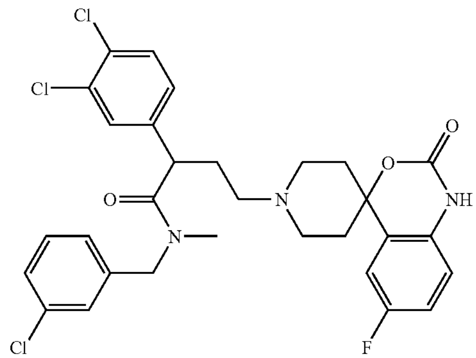 | N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (3-Chloro-benzyl)-methyl-amine (commercially available) | 606.2 |
| 20 | 600.49 | 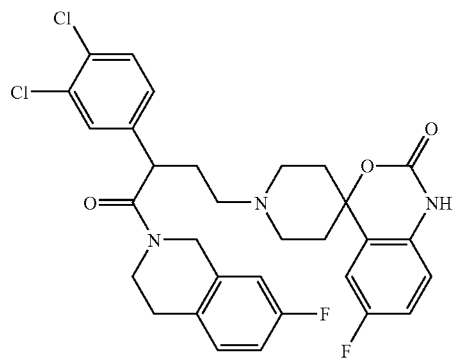 | 1'-[3-(3,4-dichlorophenyl)-4-(7-fluoro-3,4-dihydroisoquinolin-2(1H)-yl)-4-oxobutyl]-6-fluorospiro[3,1-benzoxazine-4,4'-piperidin]-2(1H)-one | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 7-Fluoro-1,2,3,4-tetrahydro-isoquinoline (commercially available) | 600.3 |
| 21 | 533.62 | 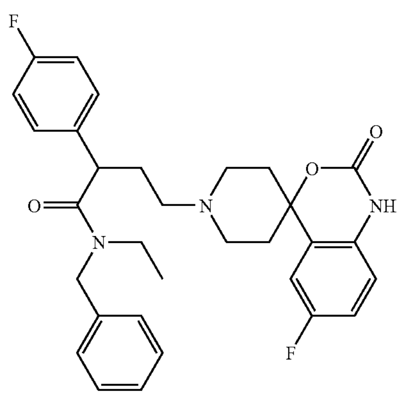 | N-benzyl-N-ethyl-4-(6-fluoro-2-oxo-1,2-dihydro-1'H-spiro[3,1-benzoxazine-4,4'-piperidin]-1'-yl)-2-(4-fluorophenyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Benzyl-ethyl-amine (commercially available) | 534.3 |
| 22 | 519.59 | 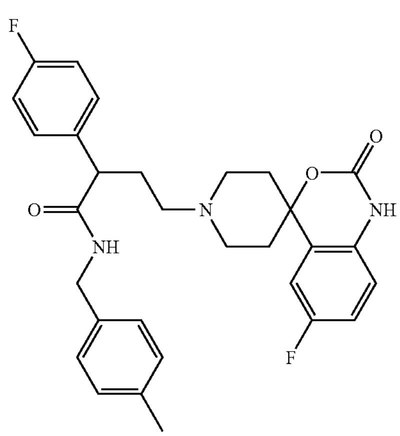 | 4-(6-fluoro-2-oxo-1,2-dihydro-1'H-spiro[3,1-benzoxazine-4,4'-piperidin]-1'-yl)-2-(4-fluorophenyl)-N-(4-methylbenzyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 4-Methyl-benzylamine (commercially available) | 520.2 |

TABLE 2-continued

| Exp | MW | Structure | Compound name | Starting materials | MW found MH+ |
|---|---|---|---|---|---|
| 23 | 540.01 | 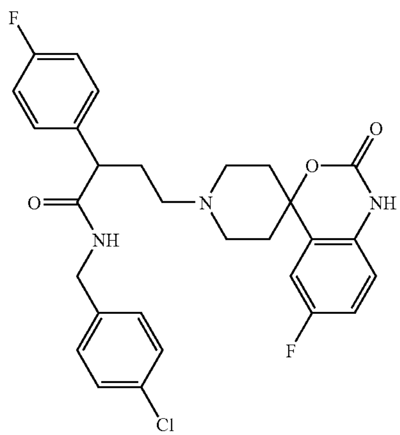 | N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 4-Chloro-benzylamine (commercially available) | 540.2 |
| 24 | 547.65 | 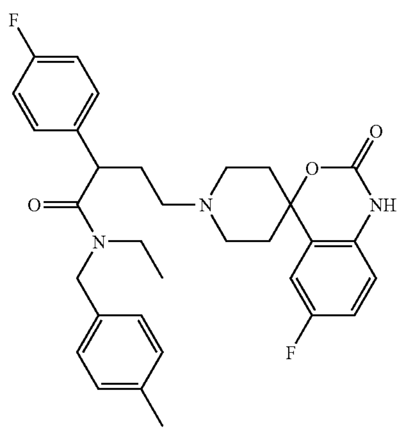 | N-ethyl-4-(6-fluoro-2-oxo-1,2-dihydro-1'H-spiro[3,1-benzoxazine-4,4'-piperidin]-1'-yl)-2-(4-fluorophenyl)-N-(4-methylbenzyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Ethyl-(4-methyl-benzyl)-amine (commercially available) | 548.3 |
| 25 | 554.04 | 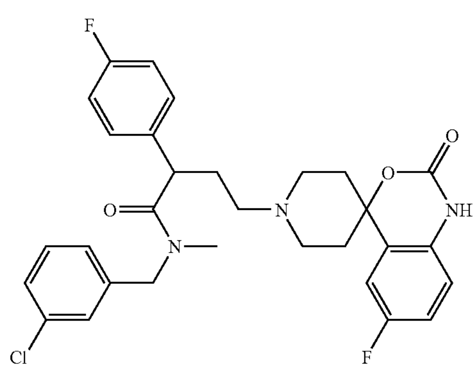 | N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (3-Chloro-benzyl)-methyl-amine (commercially available) | 554.1 |

TABLE 2-continued

| Exp | MW | Structure | Compound name | Starting materials | MW found MH+ |
|---|---|---|---|---|---|
| 26 | 554.04 | 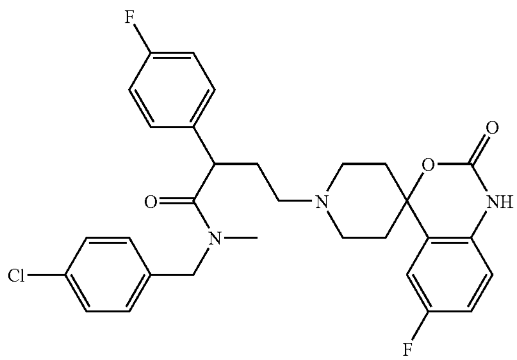 | N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (4-Chloro-benzyl)-methyl-amine (commercially available) | 554.3 |
| 27 | 554.04 | 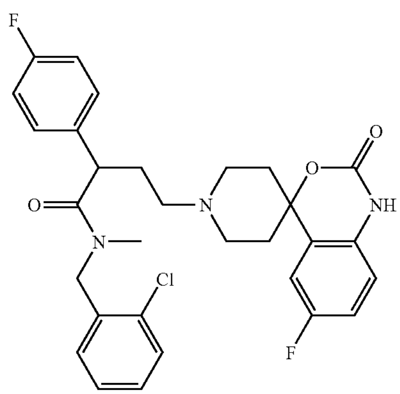 | N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (2-Chloro-benzyl)-methyl-amine (commercially available) | 554.3 |
| 28 | 576.54 | 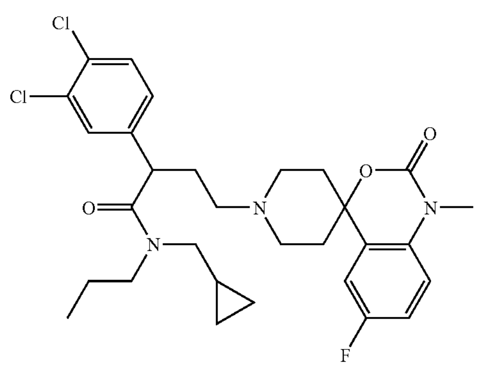 | N-(cyclopropylmethyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-propylbutanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Cyclopropylmethyl-propyl-amine (commercially available) | 576.3 |
| 29 | 598.55 | 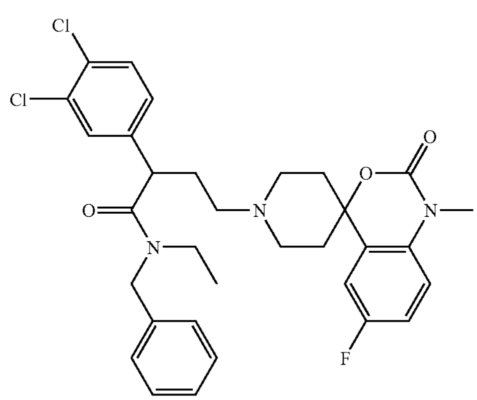 | N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Benzyl-ethyl-amine (commercially available) | 598.3 |

TABLE 2-continued

| Exp | MW | Structure | Compound name | Starting materials | MW found MH+ |
|---|---|---|---|---|---|
| 30 | 617.59 | 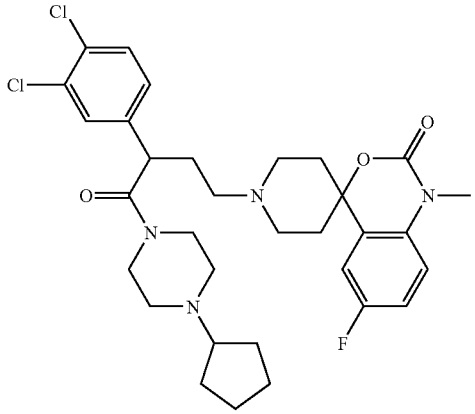 | 1'-[4-(4-cyclopentyl-piperazin-1-yl)-3-(3,4-dichlorophenyl)-4-oxobutyl]-6-fluoro-1-methylspiro[3,1-benzoxazine-4,4'-piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 1-cyclopentyl-piperazine (commercially available) | 617.5 |
| 31 | 584.52 | 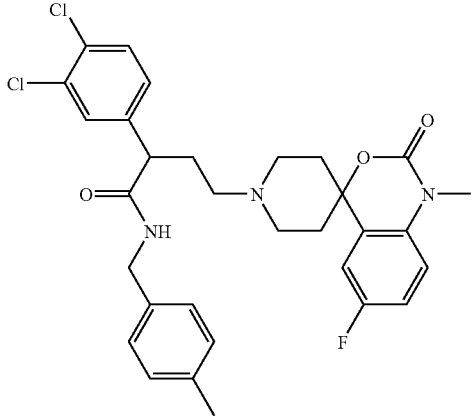 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Methyl-benzylamine (commercially available) | 584.3 |
| 32 | 570.49 | 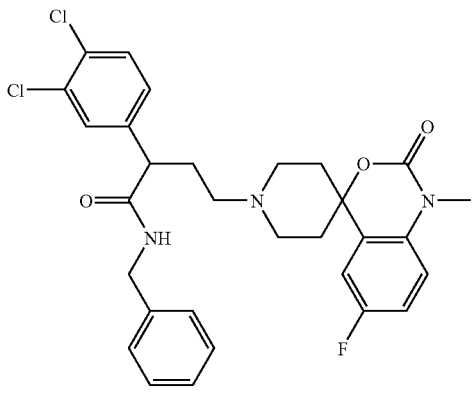 | N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Benzylamine (commercially available) | 570.3 |

TABLE 2-continued

| Exp | MW | Structure | Compound name | Starting materials | MW found MH+ |
|---|---|---|---|---|---|
| 33 | 648.58 | 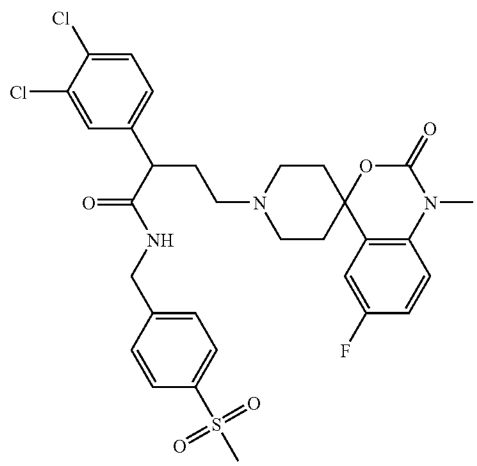 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Methanesulfonyl-benzylamine (commercially available) | 648.2 |
| 34 | 604.94 | 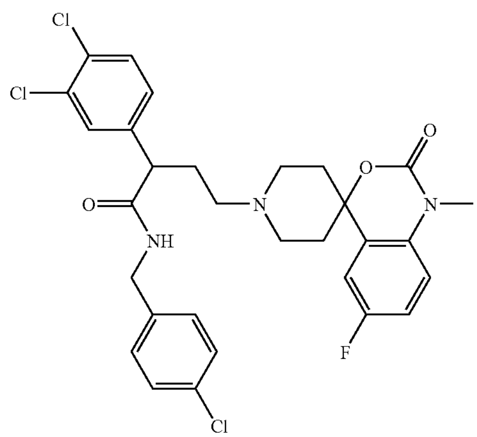 | N-(4-chlorobenzyl)-2-(3,4-dichlorophenyl)-4-(6-fluoro-1-methyl-2-oxo-1,2-dihydro-1'H-spiro[3,1-benzoxazine-4,4' piperidin]-1'-yl)-butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Chloro-benzylamine (commercially available) | 606.1 |
| 35 | 578.51 | 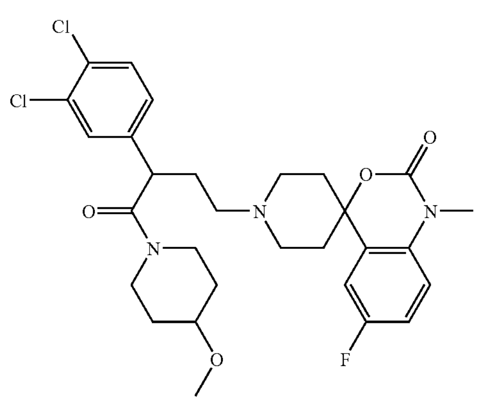 | 1'-[3-(3,4-dichlorophenyl)-4-(4-methoxypiperidin-1-yl)-4-oxobutyl]-6-fluoro-1-methylspiro[3,1-benzoxazine-4,4' piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Methoxy-piperidine (commercially available) | 578.3 |

TABLE 2-continued

| Exp | MW | Structure | Compound name | Starting materials | MW found MH+ |
|---|---|---|---|---|---|
| 36 | 536.47 | 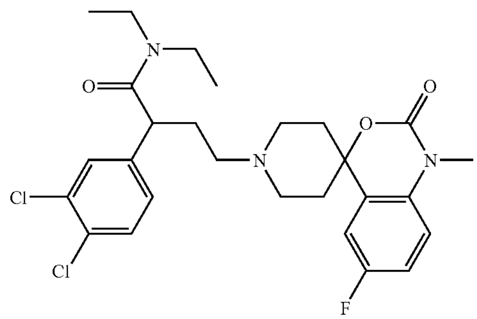 | 2-(3,4-dichlorophenyl)-N,N-diethyl-4-(6-fluoro-1-methyl-2-oxo-1,2-dihydro-1'H-spiro[3,1-benzoxazine-4,4'-piperidin]-1'-yl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and diethylamine (commercially available) | 536.3 |
| 37 | 593.53 | 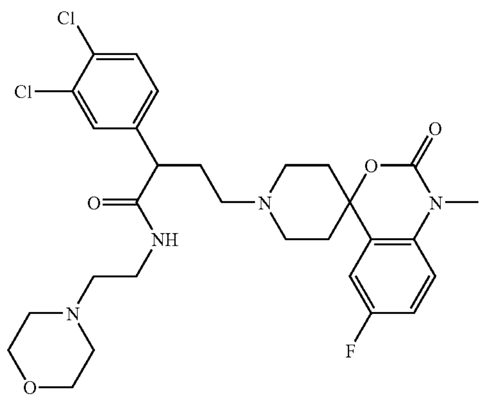 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-(2-morpholin-4-ylethyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 2-Morpholin-4-yl-ethylamine (commercially available) | 593.2 |
| 38 | 614.52 | 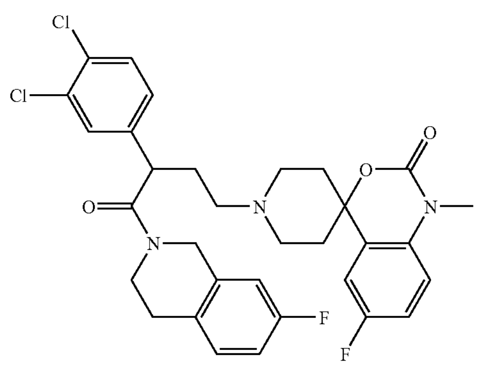 | 1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 7-Fluoro-1,2,3,4-tetrahydro-isoquinoline (commercially available) | 614.2 |
| 39 | 612.57 | 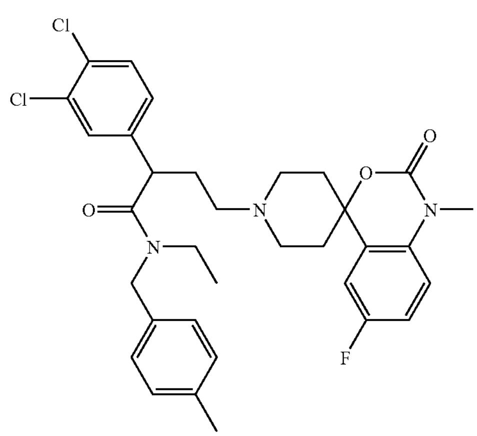 | 2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Ethyl-(4-methyl-benzyl)-amine (commercially available) | 612.3 |

TABLE 2-continued

| Exp | MW | Structure | Compound name | Starting materials | MW found MH+ |
|---|---|---|---|---|---|
| 40 | 618.96 | 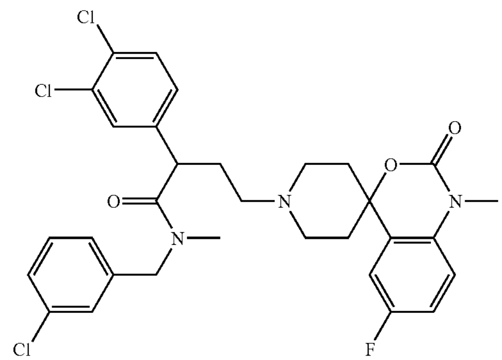 | N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (3-Chloro-benzyl)-methyl-amine (commercially available) | 618.3 |
| 41 | 562.51 | 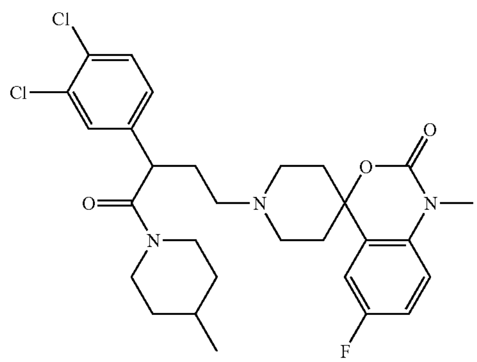 | 1'-[3-(3,4-dichlorophenyl)-4-(4-methylpiperidin-1-yl)-4-oxobutyl]-6-fluoro-1-methylspiro[3,1-benzoxazine-4,4'-piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Methylpiperidine (commercially available) | 562.1 |
| 42 | 618.96 | 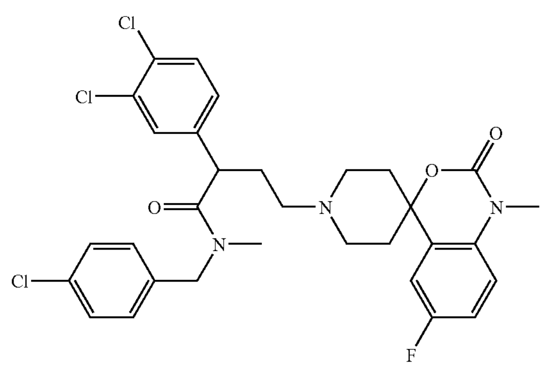 | N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (4-Chloro-benzyl)-methyl-amine (commercially available) | 618.3 |
| 43 | 566.48 | 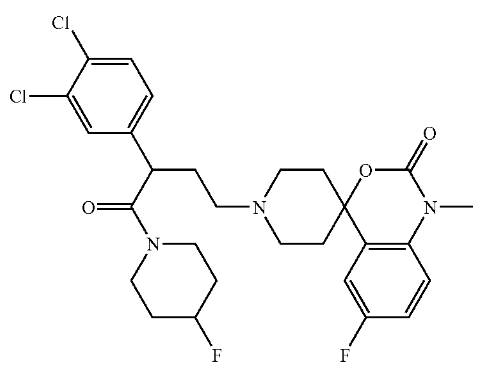 | 1'-[3-(3,4-dichlorophenyl)-4-(4-fluropiperidin-1-yl)-4-oxobutyl]-6-fluoro-1-methylspiro[3,1-benzoxazine-4,4'-piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Fluoro-piperidine (commercially available) | 566.2 |

TABLE 2-continued

| Exp | MW | Structure | Compound name | Starting materials | MW found MH+ |
|---|---|---|---|---|---|
| 44 | 618.96 | 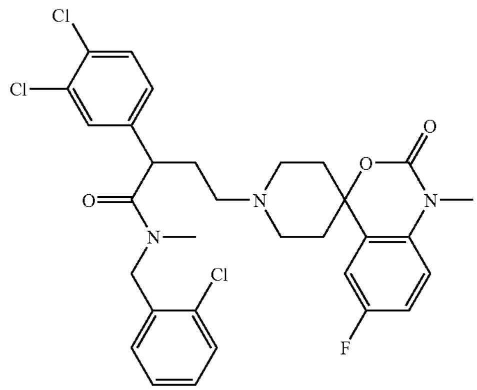 | N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (2-Chloro-benzyl)-methyl-amine (commercially available) | 618.3 |
| 45 | 627.56 | 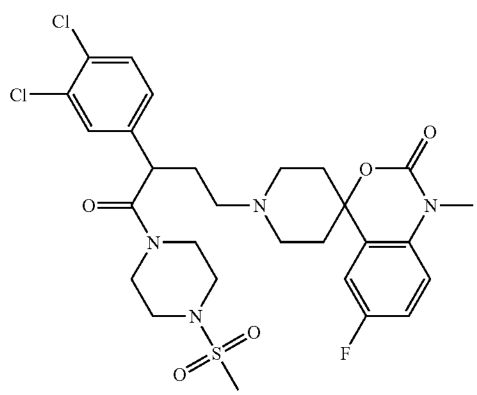 | 1'-{3-(3,4-dichlorophenyl)-4-[4-(methylsulfonyl)piperazin-1-yl]-4-oxobutyl}-6-fluoro-1-methylspiro[3,1-benzoxazine-4,4'-piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 1-Methanesulfonyl piperazine (commercially available) | 627.3 |
| 46 | 625.57 | 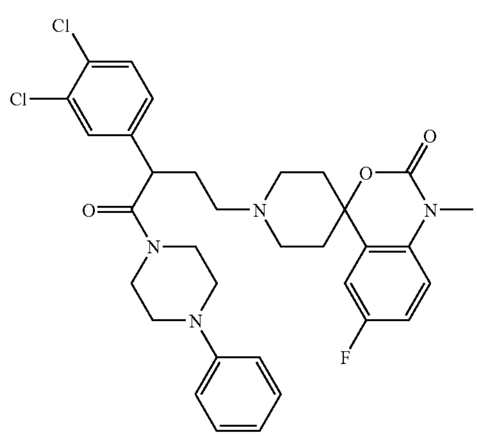 | 1'-[3-(3,4-dichlorophenyl)-4-oxo-4-(4-phenylpiperazin-1-yl)butyl]-6-fluoro-1-methylspiro[3,1-benzoxazine-4,4'-piperidin]-2(1H)-one | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 1-Phenyl-piperazine (commercially available) | 627.3 |

TABLE 2-continued

| Exp | MW | Structure | Compound name | Starting materials | MW found MH+ |
|---|---|---|---|---|---|
| 47 | 574.45 | 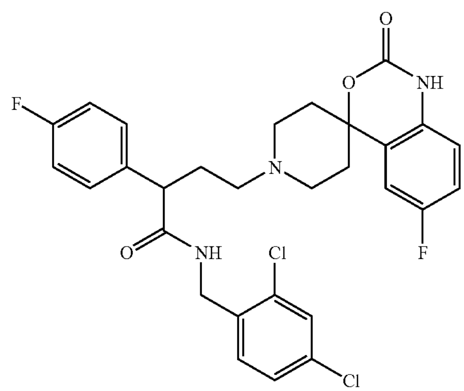 | N-(2,4-dichlorobenzyl)-4-(6-fluoro-2-oxo-1,2-dihydro-1'H-spiro[3,1-benzoxazine-4,4'-piperidin]-1'-yl)-2-(4-fluorophenyl)butanamide. | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 2,4-Dichloro-benzylamine (commercially available) | 576.2 |
| 48 | 533.62 | 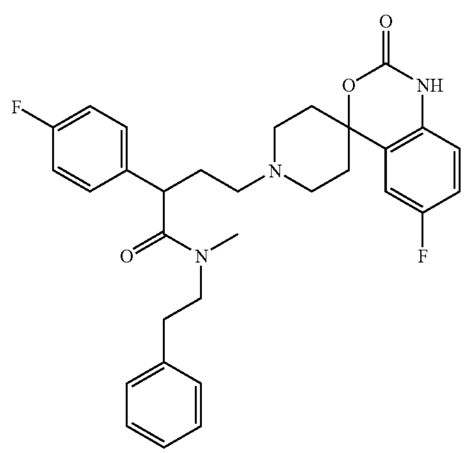 | 4-(6-fluoro-2-oxo-1,2-dihydro-1'H-spiro[3,1-benzoxazine-4,4'-piperidin]-1'-yl)-2-(4-fluorophenyl)-N-methyl-N-(2-phenylethyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Methyl-phenethyl-amine (commercially available) | 534.2 |
| 49 | 589.56 | 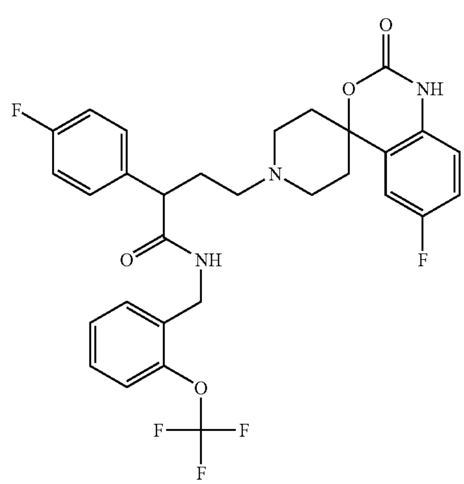 | 4-(6-fluoro-2-oxo-1,2-dihydro-1'H-spiro[3,1-benzoxazine-4,4'-piperidin]-1'-yl)-2-(4-fluorophenyl)-N-(trifluoromethoxy)benzyl]butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 2-Trifluoromethoxy-benzylamine (commercially available) | 590.3 |

TABLE 2-continued

| Exp | MW | Structure | Compound name | Starting materials | MW found MH+ |
|---|---|---|---|---|---|
| 50 | 571.57 | 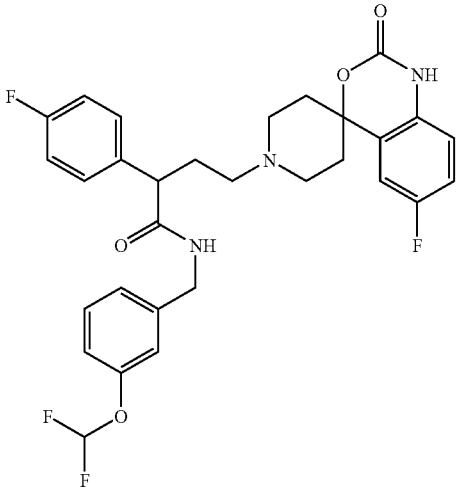 | N-[3-(difluoromethoxy)benzyl]-4-(6-fluoro-2-oxo-1,2-dihydro-1'H-spiro[3,1-benzoxazine-4,4'-piperidin]-1'-yl)-2-(4-fluorophenyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 3-Difluoromethoxy-benzylamine (commercially available) | 572.3 |
| 51 | 587.59 | 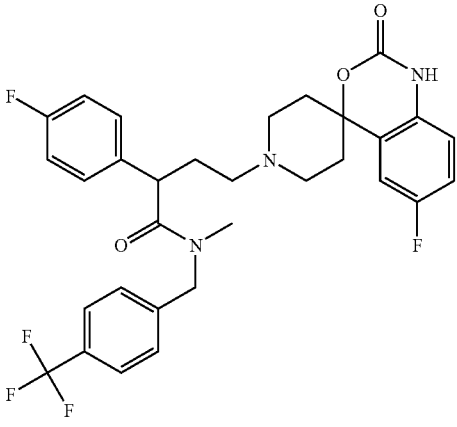 | 4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Methyl-(4-trifluoromethyl-benzyl)-amine (commercially available) | 588.2 |
| 52 | 596.68 | 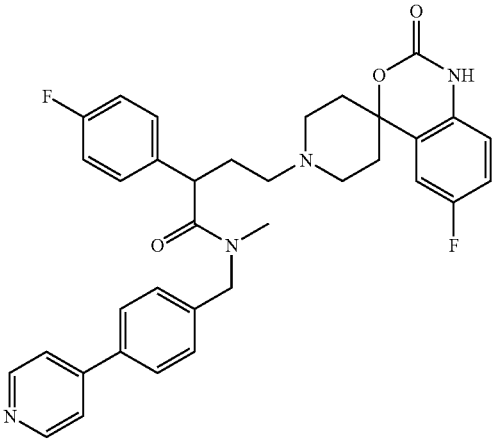 | 4-(6-fluoro-2-oxo-1,2-dihydro-1'H-spiro[3,1-benzoxazine-4,4'-piperidin]-1'-yl)-2-(4-fluorophenyl)-N-methyl-N-(4-pyridin-4-ylbenzyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Methyl-(4-pyridin-4-yl-benzyl)-amine (commercially available) | 597.4 |

TABLE 2-continued

| Exp | MW | Structure | Compound name | Starting materials | MW found MH+ |
|---|---|---|---|---|---|
| 53 | 567.61 | 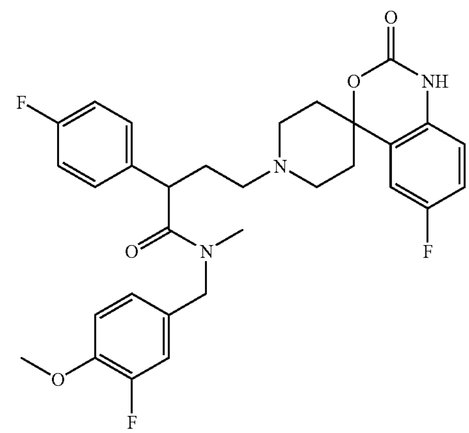 | N-(3-fluoro-4-methoxybenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (3-Fluoro-4-methoxy-benzyl)-methyl-amine (commercially available) | 568.3 |
| 54 | 615.62 | 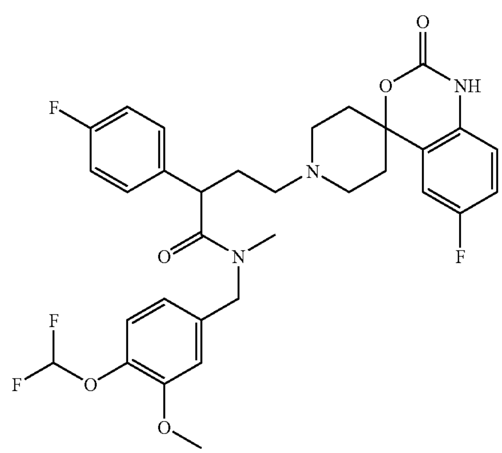 | N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (4-Difluoromethoxy-(3-methoxy-benzyl)-methyl-amine (commercially available) | 616.3 |
| 55 | 537.58 | 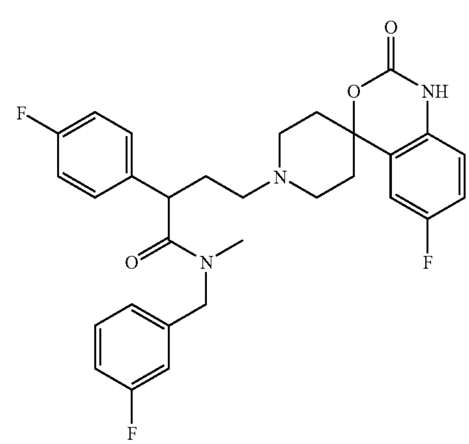 | N-(3-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (3-Fluoro-benzyl)-methyl-amine (commercially available) | 538.4 |

TABLE 2-continued

| Exp | MW | Structure | Compound name | Starting materials | MW found MH+ |
|---|---|---|---|---|---|
| 56 | 533.62 | 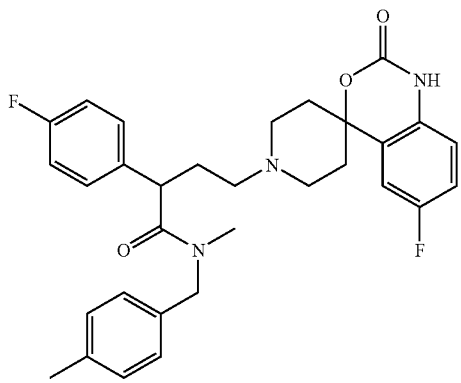 | 4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Methyl-(4-methyl benzyl)-amine (commercially available) | 534.2 |
| 57 | 589.56 | 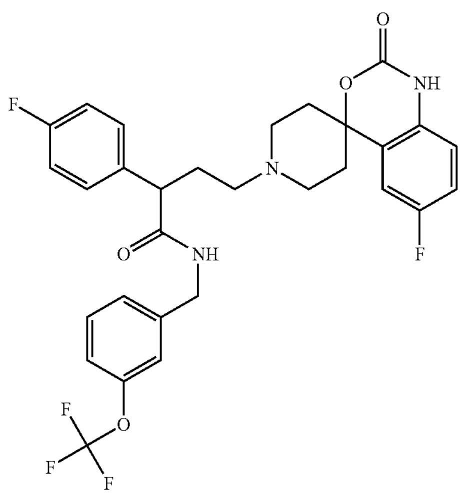 | 4-(6-fluoro-2-oxo-1,2-dihydro-1'H-spiro[3,1-benzoxazine-4,4'-piperidin]-1'-yl)-2-(4-fluorophenyl)-N-[3-(trifluoromethoxy)benzyl]butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 3-Trifluoromethoxy-benzylamine (commercially available) | 590.3 |
| 58 | 587.59 | 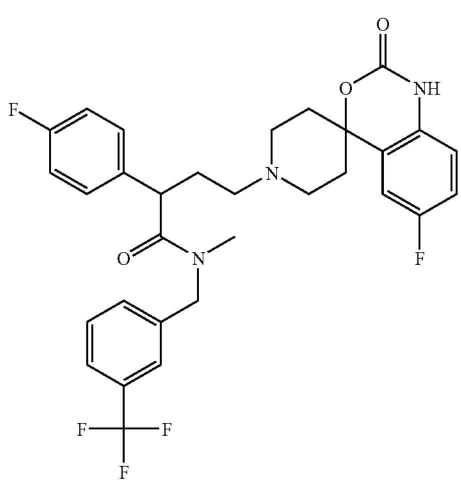 | 4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethoxy)benzyl]butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and Methyl-(3-trifluoromethyl-benzyl)-amine (commercially available) | 588.3 |

TABLE 2-continued

| Exp | MW | Structure | Compound name | Starting materials | MW found MH+ |
|---|---|---|---|---|---|
| 59 | 537.58 | 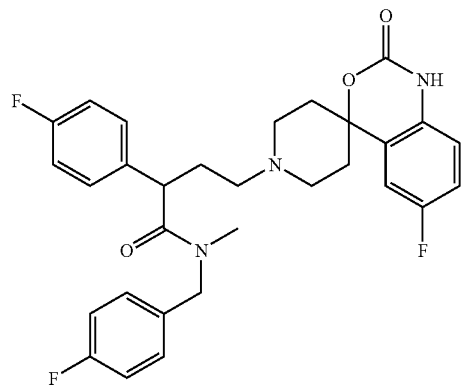 | N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and (4-Fluoro-benzyl)-methyl-amine (commercially available) | 538.5 |
| 60 | 523.55 | 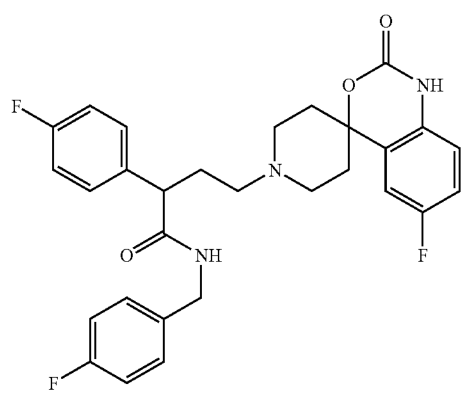 | N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 4-Fluoro-benzylamine (commercially available) | 524.5 |
| 61 | 573.56 | 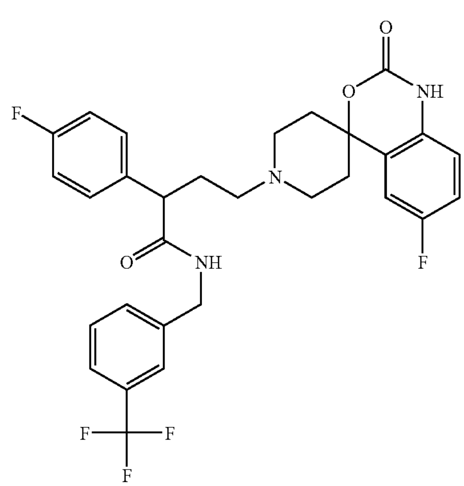 | 4-(6-fluoro-2-oxo-1,2-dihydro-1'H-spiro[3,1-benzoxazine-4,4'-piperidin]-1'-yl)-2-(4-fluorophenyl)-N-[3-(trifluoromethyl)benzyl]butanamide | 2-(4-fluorophenyl)-4-(6-fluoro-2-oxo-1,2-dihydro-1'H-spiro[3,1-benzoxazine-4,4'-piperidin]-1'-yl)butanoic acid, hydrochloride (intermediate 4) and 3-Trifluoromethyl-benzylamine (commercially available) | 574.5 |

TABLE 2-continued

| Exp | MW | Structure | Compound name | Starting materials | MW found MH+ |
|---|---|---|---|---|---|
| 62 | 625.35 | 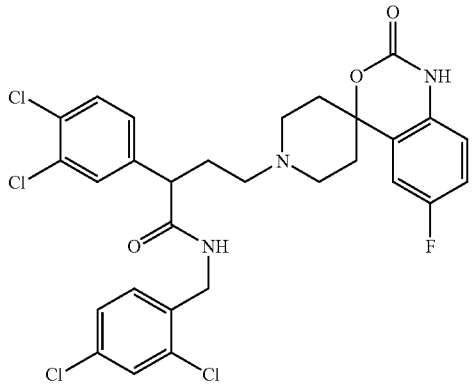 | N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide | 22-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 2,4-Dichloro-benzylamine (commercially available) | 626.1 |
| 63 | 671 | 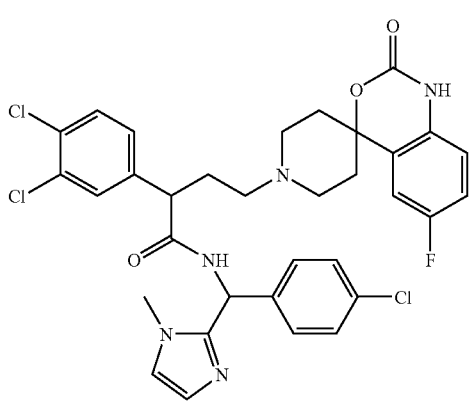 | N-[(4-chlorophenyl)(1-methyl-1H-imidazol-2-yl)methyl]-2-(3,4-dichlorophenyl)-4-(6-fluoro-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and C-(4-Chloro-phenyl)-C-(1-methyl-1H-imidazol-2-yl)-methylamine (commercially available) | 670.2 |
| 64 | 570.49 | 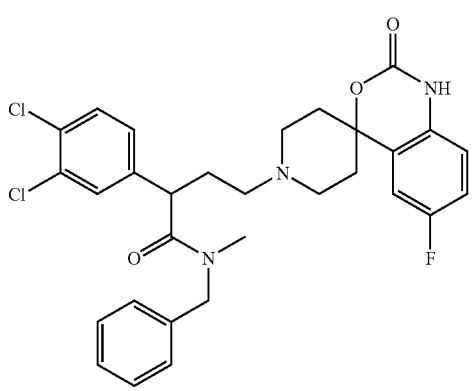 | N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Benzyl-methyl-amine (commercially available) | 570.3 |

TABLE 2-continued

| Exp | MW | Structure | Compound name | Starting materials | MW found MH+ |
|---|---|---|---|---|---|
| 65 | 584.52 | 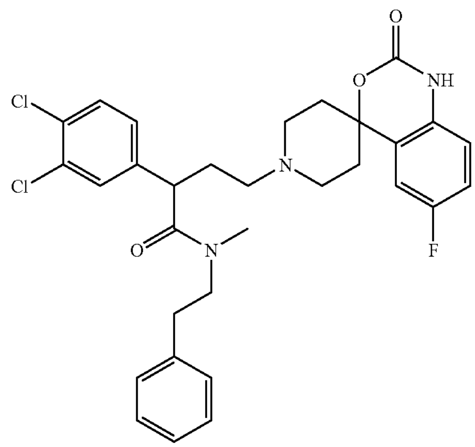 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-phenethyl-amine (commercially available) | 586.3 |
| 66 | 640.46 | 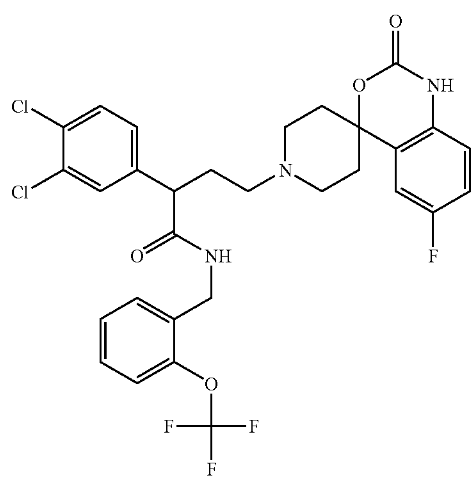 | 2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 2-Trifluoromethoxy-benzylamine (commercially available) | 640.2 |
| 67 | 622.47 | 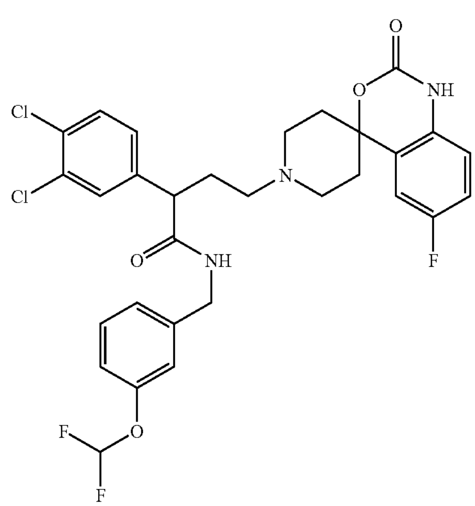 | 2-(3,4-dichlorophenyl)-N-[3-(difluoromethoxy)benzyl]4-(6-fluoro-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 3-Difluoromethoxy- (commercially available) | 622.3 |

TABLE 2-continued

| Exp | MW | Structure | Compound name | Starting materials | MW found MH+ |
|---|---|---|---|---|---|
| 68 | 638.49 | 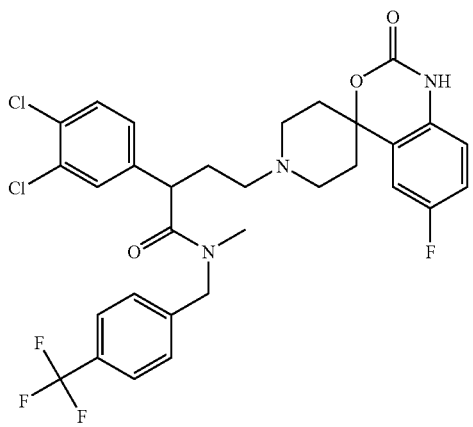 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-(4-trifluoromethyl-benzyl)-amine (commercially available) | 638.2 |
| 69 | 622.53 | 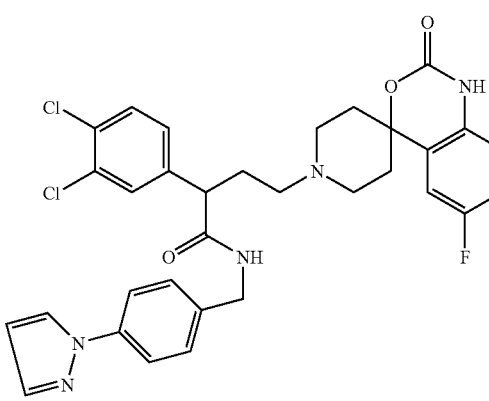 | 2-(3,4-dichlorophenyl)-4-(6-fluoro-2-oxo-1,2-dihydro-1'H-spiro[3,1-benzoxazine-4,4'-piperidin]-1'-yl)-N-[4-(1H-pyrazol-1-yl)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Pyrazol-1-yl-benzylamine (commercially available) | 622.4 |
| 70 | 655.6 | 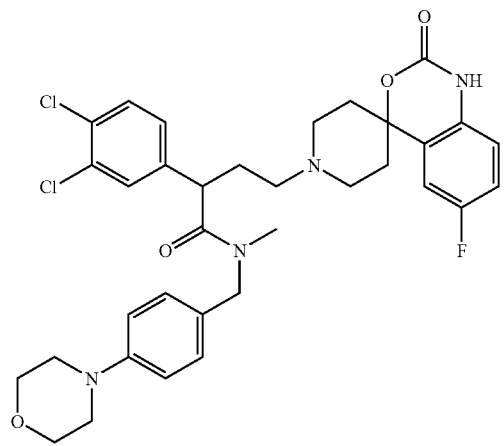 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-(4-morpholin-4-yl-benzyl)-amine (commercially available) | 655.4 |

TABLE 2-continued

| Exp | MW | Structure | Compound name | Starting materials | MW found MH+ |
|---|---|---|---|---|---|
| 71 | 653.63 | 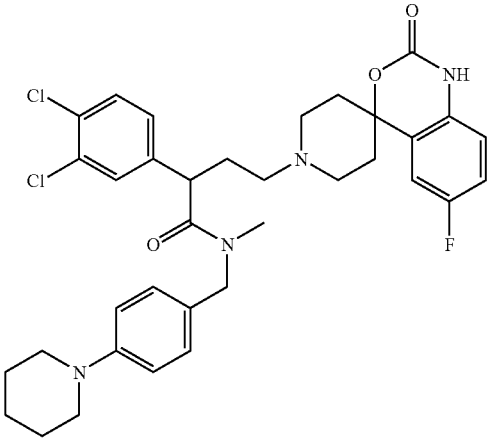 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-piperidin-1-ylbenzyl) butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-(4-piperidin-1-yl-benzyl)-amine (commercially available) | 653.4 |
| 72 | 647.58 | 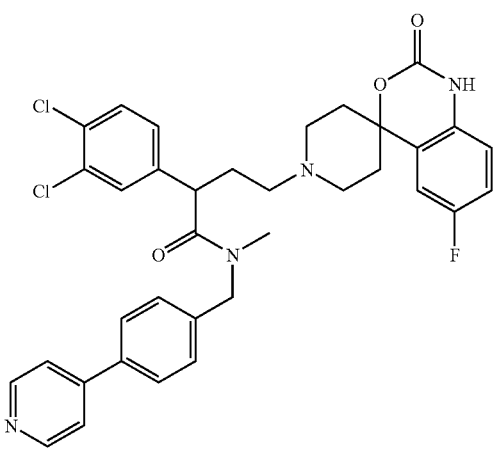 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl) butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-(4-piperidin-4-yl-benzyl)-amine (commercially available) | 647.5 |
| 73 | 652.55 | 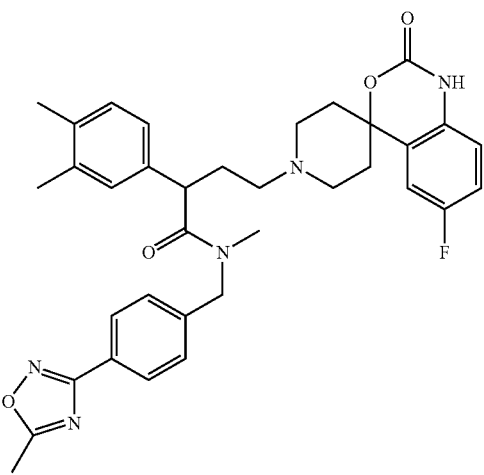 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(5-methyl-1,2,4-oxadiazol-3-yl)benzyl] butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-[4-(5-methyl[1,2,4]oxadiazol-3-yl)-benzyl]-amine (commercially available) | 652.3 |

TABLE 2-continued

| Exp | MW | Structure | Compound name | Starting materials | MW found MH+ |
|---|---|---|---|---|---|
| 74 | 618.51 | 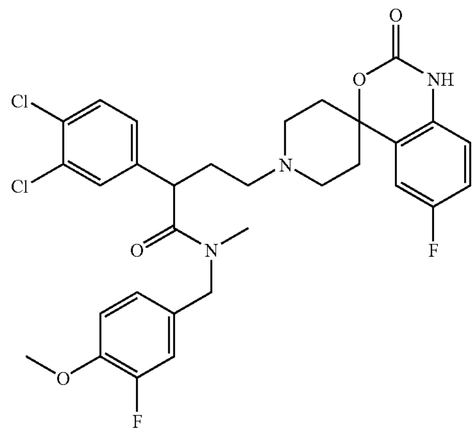 | 2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (3-Fluoro-4-methoxy-benzyl)-methyl-amine (commercially available) | 618.4 |
| 75 | 666.52 | 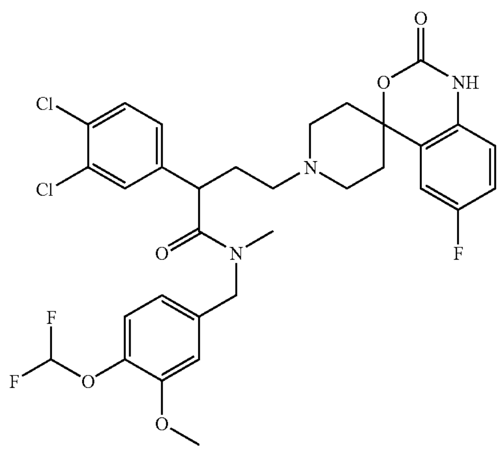 | 2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (4-Difluoromethoxy-3-methoxy-benzyl)-methyl-amine (commercially available) | 666.3 |
| 76 | 588.48 | 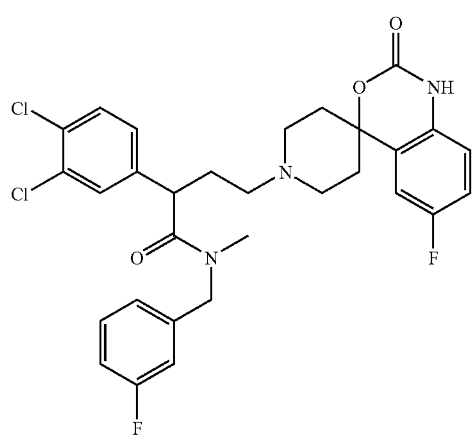 | 2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methyl-N-(4-methylbenzyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (3-Fluoro-benzyl)-methyl-amine (commercially available) | 588.1 |

TABLE 2-continued

| Exp | MW | Structure | Compound name | Starting materials | MW found MH+ |
|---|---|---|---|---|---|
| 77 | 584.52 | 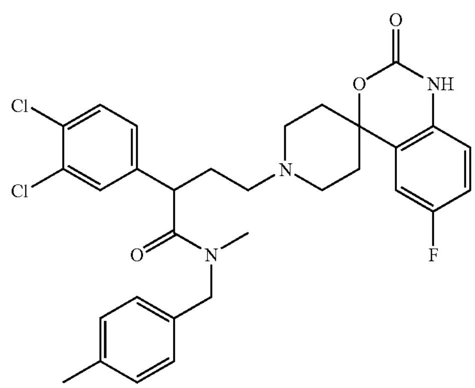 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-(4-methyl-benzyl)-amine (commercially available) | 586.2 |
| 78 | 640.46 | 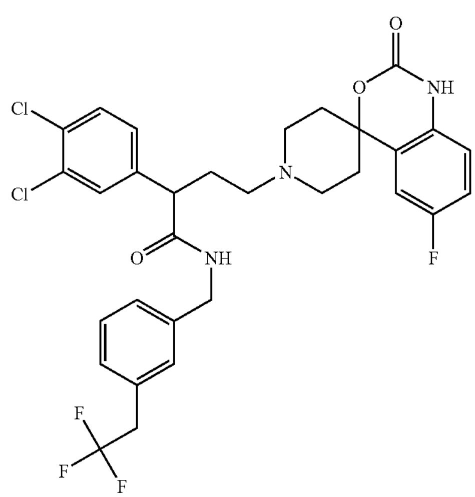 | 2-(3,4-dichlorophenyl)-4-(6-fluoro-2-oxo-1,2-dihydro-1'H-spiro[3,1-benzoxazine-4,4'-piperidin]-1'-yl)-N-[(3-trifluoromethoxy)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 3-Trifluoromethoxy-benzylamine (commercially available) | 640.2 |
| 79 | 638.49 | 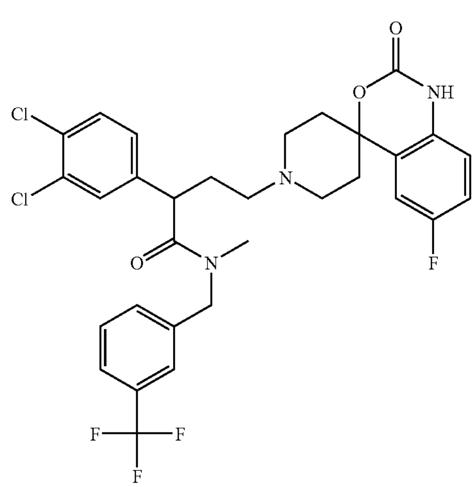 | 2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and Methyl-(3-trifluoromethyl-benzyl)-amine (commercially available) | 638.3 |

TABLE 2-continued

| Exp | MW | Structure | Compound name | Starting materials | MW found MH+ |
|---|---|---|---|---|---|
| 80 | 588.48 | 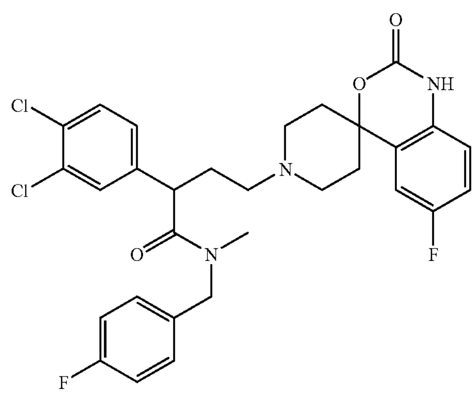 | 2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (4-Fluoro-benzyl)-methyl-amine (commercially available) | 588.1 |
| 81 | 574.45 | 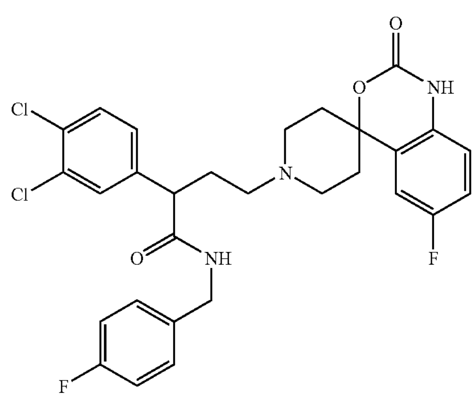 | 2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-butanamide. | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Fluoro-benzylamine (commercially available) | 576.3 |
| 82 | 586.49 | 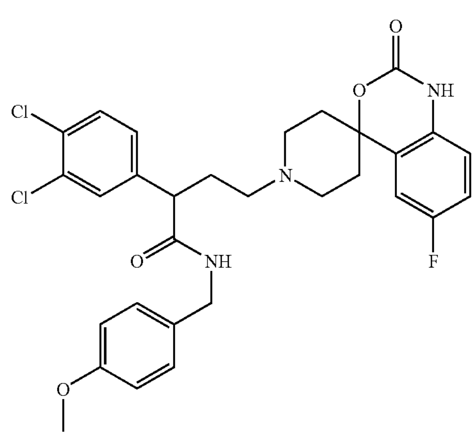 | 2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Methoxy-benzylamine (commercially available) | 586.3 |

TABLE 2-continued

| Exp | MW | Structure | Compound name | Starting materials | MW found MH+ |
|---|---|---|---|---|---|
| 83 | 624.46 | 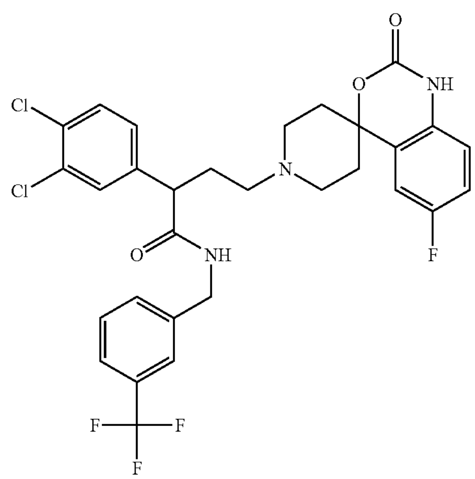 | 2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 3-Trifluoromethyl-benzylamine (commercially available) | 624.3 |
| 84 | 640.56 | 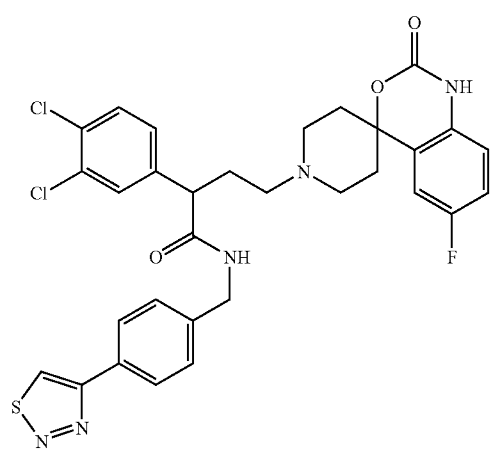 | 2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-[1,2,3]Thiadiazol-4-yl-benzylamine (commercially available) | 640.2 |
| 85 | 640.46 | 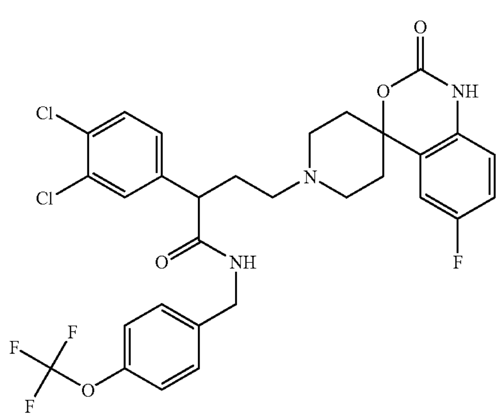 | 2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 3-Trifluoromethoxy-benzylamine (commercially available) | 640.2 |

TABLE 2-continued

| Exp | MW | Structure | Compound name | Starting materials | MW found MH+ |
|---|---|---|---|---|---|
| 86 | 581.47 | 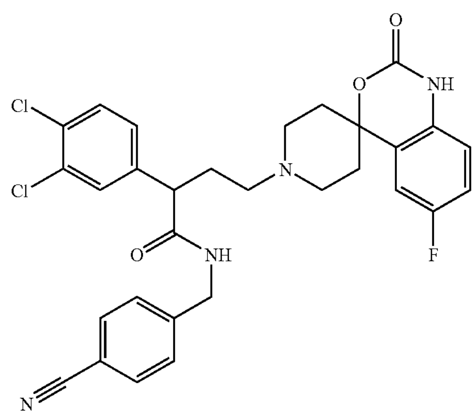 | N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and 4-Aminomethyl-benzonitrile (commercially available) | 581.3 |
| 87 | 639.38 | 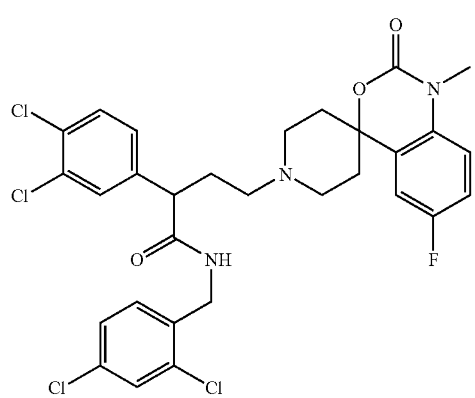 | N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 2,4-Dichloro-benzylamine (commercially available) | 640.3 |
| 88 | 685.03 | 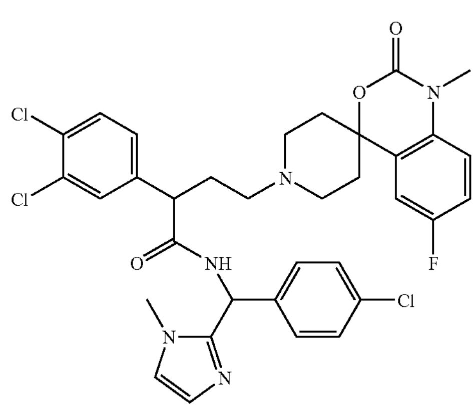 | N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 5) and C-(4-Chloro-phenyl)-C-(1-methyl-1H-imidazol-2-yl)-methylamine (commercially available) | 686.4 |

TABLE 2-continued

| Exp | MW | Structure | Compound name | Starting materials | MW found MH+ |
|---|---|---|---|---|---|
| 89 | 584.52 | 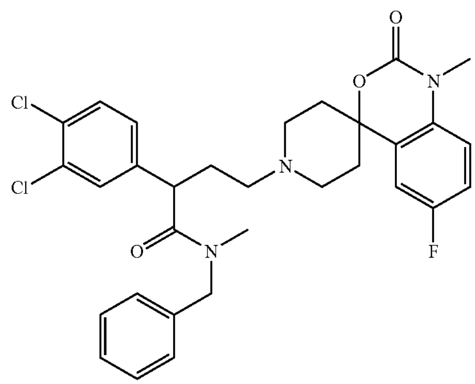 | N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 5) and Benzyl-methyl-amine (commercially available) | 586.3 |
| 90 | 598.55 | 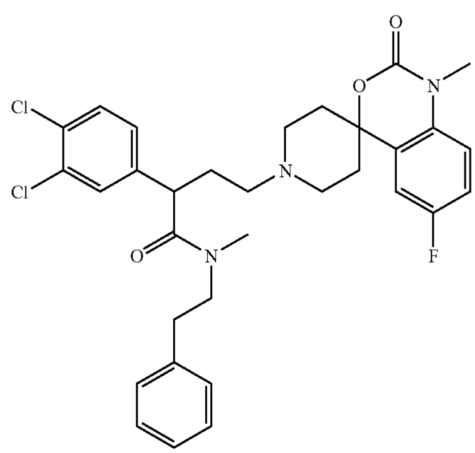 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-metyl-N-(2-phenylethyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-phenethyl-amine (commercially available) | 598.3 |
| 91 | 654.49 | 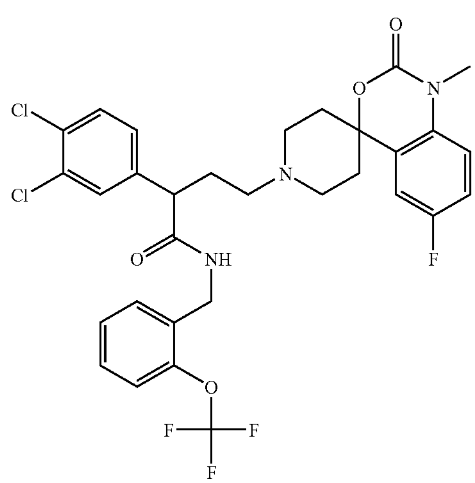 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 2-Trifluoromethoxy-benzylamine (commercially available) | 654.3 |

TABLE 2-continued

| Exp | MW | Structure | Compound name | Starting materials | MW found MH+ |
|---|---|---|---|---|---|
| 92 | 636.5 | 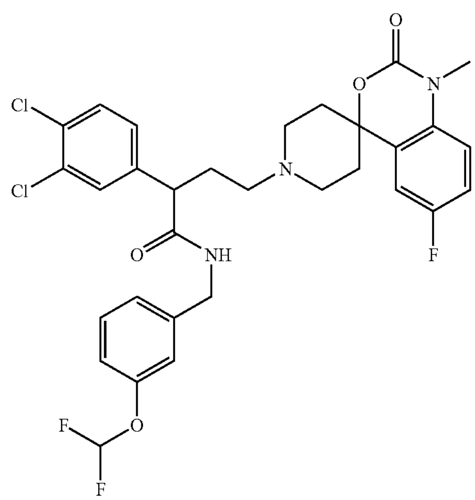 | 2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 3-Difluoromethoxy-benzylamine (commercially available) | 636.3 |
| 93 | 652.52 | 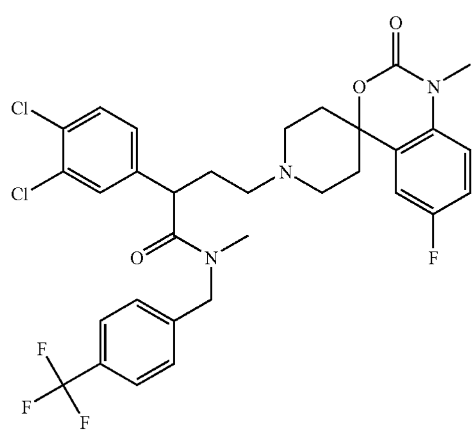 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-(4-trifluoromethyl-benzyl)-amine (commercially available) | 652.3 |
| 94 | 636.55 | 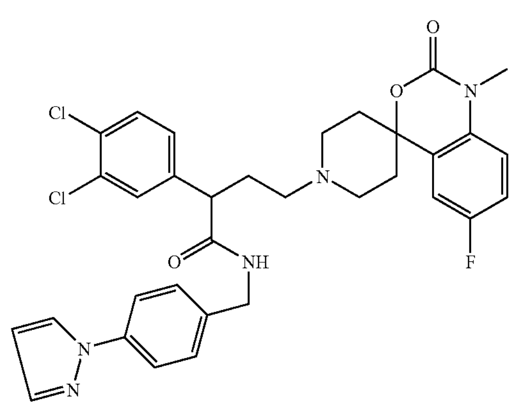 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Pyrazol-1-yl-benzylamine (commercially available) | 636.3 |

TABLE 2-continued

| Exp | MW | Structure | Compound name | Starting materials | MW found MH+ |
|---|---|---|---|---|---|
| 95 | 669.62 | 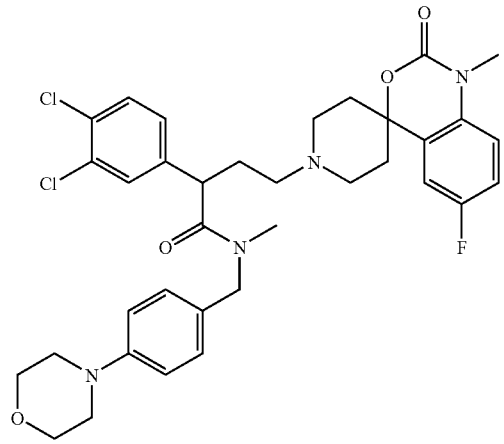 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-(4-morpholin-4-yl-benzyl)-amine (commercially available) | 669.4 |
| 96 | 667.65 | 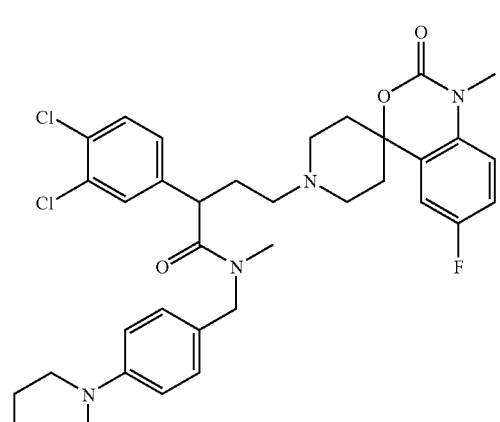 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-piperidin-1-ylbenzyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-(4-piperidin-1-yl-benzyl)-amine (commercially available) | 667.3 |
| 97 | 661.6 | 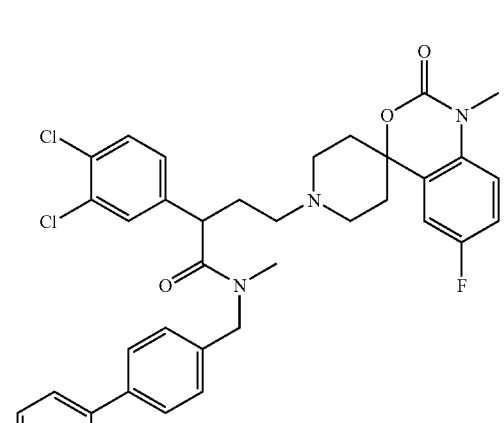 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-(4-piperidin-1-yl-benzyl)-amine (commercially available) | 661.4 |

TABLE 2-continued

| Exp | MW | Structure | Compound name | Starting materials | MW found MH+ |
|---|---|---|---|---|---|
| 98 | 666.58 | 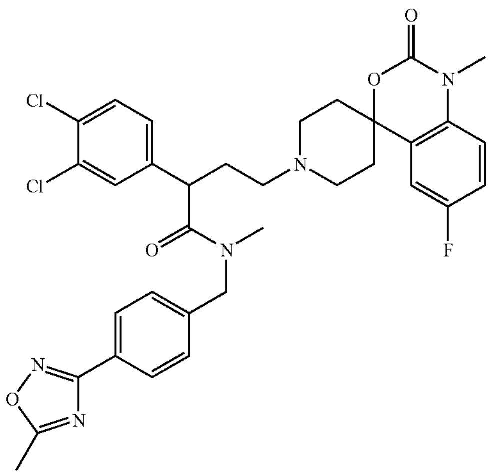 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(5-methyl-1,2,4-oxadiazol-3-yl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-[4-(5-methyl-[1,2,4]oxadiazol-3-yl)-benzyl]-amine (commercially available) | 666.3 |
| 99 | 632.53 | 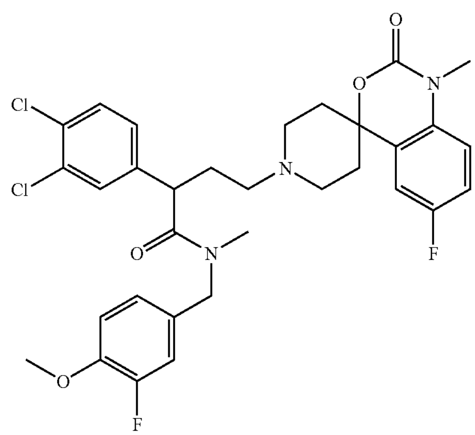 | 2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methyl-butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (3-Fluoro-4-methoxy-benzyl)-methyl-amine (commercially available) | 632.5 |
| 100 | 680.55 | | 2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methyl-butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 5) and (4-Difluoro-methoxy-3-methoxy-benzyl)-methyl-amine (commercially available) | 680.3 | ns

TABLE 2-continued

| Exp | MW | Structure | Compound name | Starting materials | MW found MH+ |
|---|---|---|---|---|---|
| 101 | 602.51 | 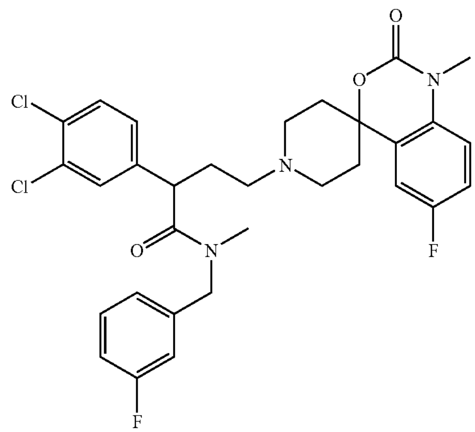 | 2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methyl-butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (3-Fluoro-benzyl)-methyl-amine (commercially available) | 604.3 |
| 102 | 598.55 | 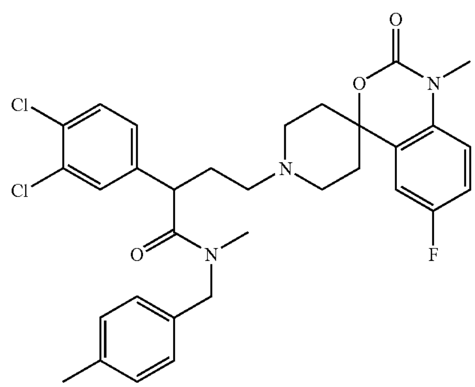 | 2-(3,4-dichlorophenyl)-fluoro-1-methyl-2-oxo-1,2-dihydro-1'H-spiro[3,1-benzoxazine-4,4'-piperidin]-1'-yl)-N-methyl-N-(4-methylbenzyl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-(4-methyl-benzyl)-amine (commercially available) | 598.3 |
| 103 | 654.49 | 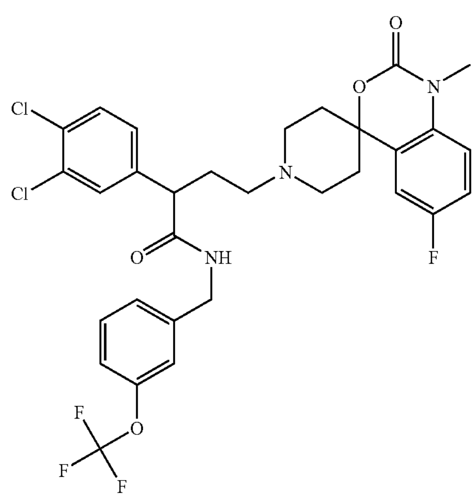 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 3-Trifluoromethoxy-benzylamine (commercially available) | 654.4 |

TABLE 2-continued

| Exp | MW | Structure | Compound name | Starting materials | MW found MH+ |
|---|---|---|---|---|---|
| 104 | 652.52 | 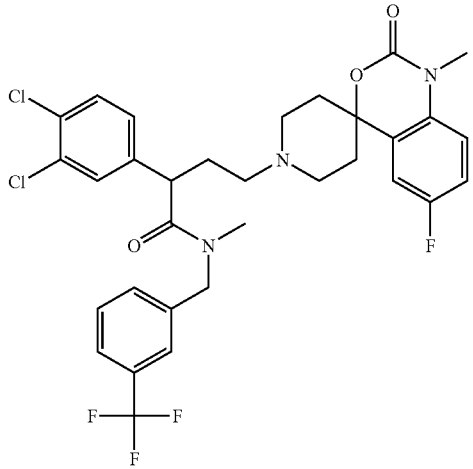 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and Methyl-(3-trifluoromethyl-benzyl)-amine (commercially available) | 652.3 |
| 105 | 602.51 | 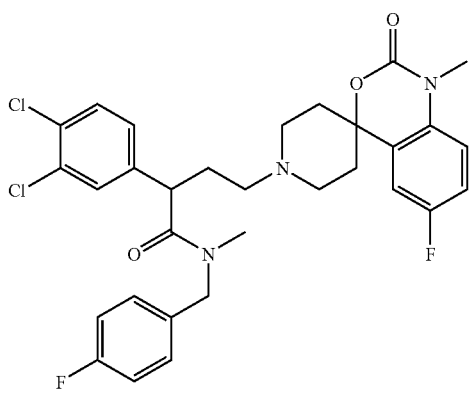 | 2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methyl-butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (4-Fluoro-benzyl)-methyl-amine (commercially available) | 604.3 |
| 106 | 588.48 | 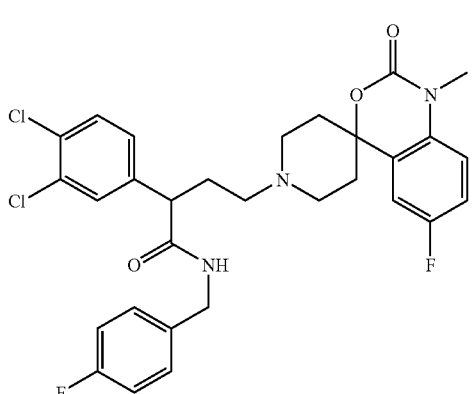 | 2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-butanamide | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 5) and 4-Fluoro-benzylamine (commercially available) | 588.1 |

TABLE 2-continued

| Exp | MW | Structure | Compound name | Starting materials | MW found MH+ |
|---|---|---|---|---|---|
| 107 | 600.52 | 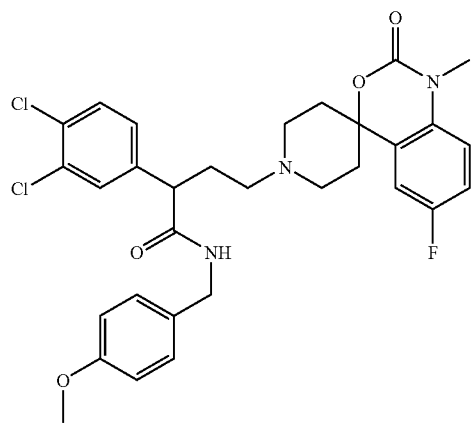 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide | 2-(3,4-dichlorophenyl)-4-(6-fluoro-1-methyl-2-oxo-1,2-dihydro-1'H-spiro[3,1-benzoxazine-4,4'H-piperidin]-1'-yl)butanoic acid, hydrochloride (intermediate 5) and 4-Methoxy-benzylamine (commercially available) | 600.3 |
| 108 | 638.49 | 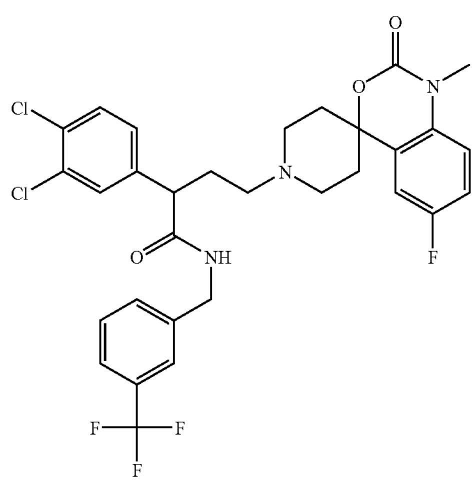 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 3-Trifluoromethyl-benzylamine (commercially available) | 638.3 |
| 109 | 654.59 | 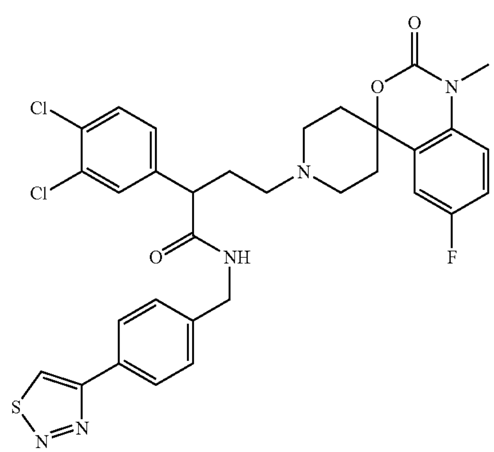 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-[1,2,3]Thiadiazol-4-yl-benzylamine (commercially available) | 654.4 |

TABLE 2-continued

| Exp | MW | Structure | Compound name | Starting materials | MW found MH+ |
|---|---|---|---|---|---|
| 110 | 654.49 | 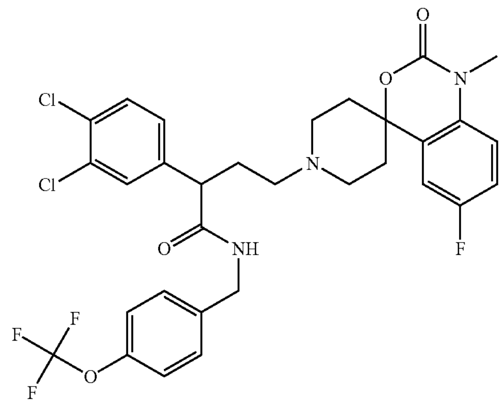 | 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Trifluoromethoxy-benzylamine (commercially available) | 654.4 |
| 111 | 595.5 | 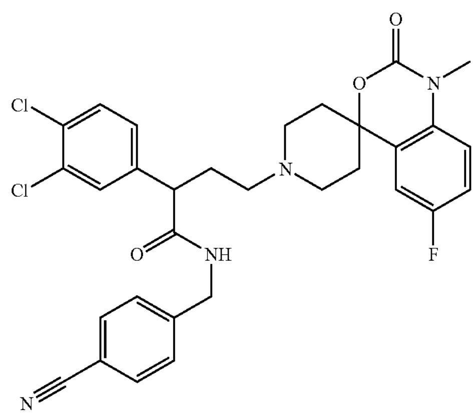 | N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and 4-Aminomethyl-benzonitrile (commercially available) | 595.4 |
| 112 | 584.52 | 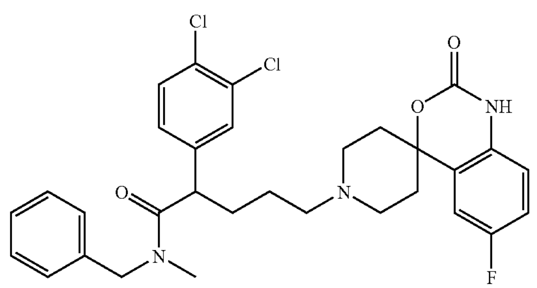 | N-benzyl-2-(3,4-dichlorophenyl)-5-(6-fluoro-2-oxo-1,2-dihydro-1'H-spiro[3,1-benzoxazine-4,4'-piperidin]-1'-yl)-N-methyl-pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Benzyl-methyl-amine (commercially available) | 584.2 |
| 113 | 639.38 | 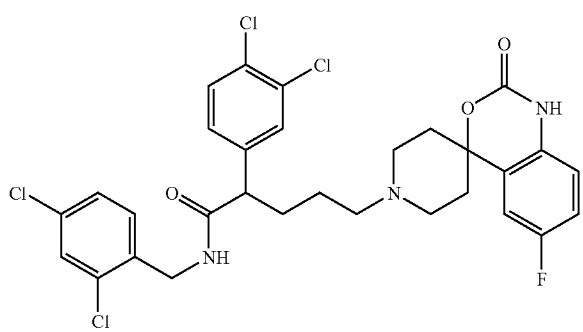 | N-(2,4-dichloro-benzyl)-2-(3,4-dichlorophenyl)-5-(6-fluoro-2-oxo-1,2-dihydro-1'H-spiro[3,1-benzoxazine-4,4'-piperidin]-1'-yl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 2,4-Dichloro-benzylamine (commercially available) | 640.3 |

TABLE 2-continued

| Exp | MW | Structure | Compound name | Starting materials | MW found MH+ |
|---|---|---|---|---|---|
| 114 | 685.03 | 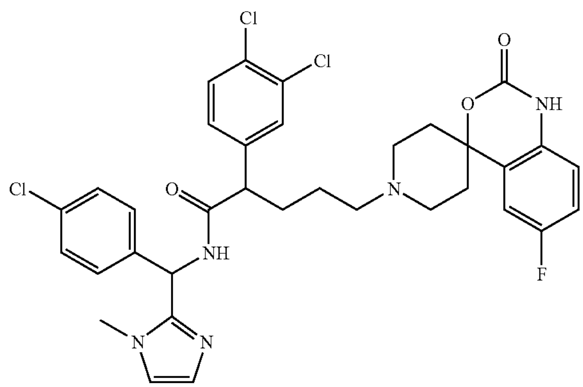 | N-[(4-chlorophenyl)(1-methyl-1H-imidazol-2-yl)methyl]-2-(3,4-dichlorophenyl)-5-(6-fluoro-2-oxo-1,2-dihydro-1'H-spiro[3,1-benzoxazine-4,4'-piperidin]-1'-yl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and C-(4-Chloro-phenyl)-C-(1-methyl-1H-imidazol-2-yl)-methylamine (commercially available) | 686.3 |
| 115 | 618.96 | 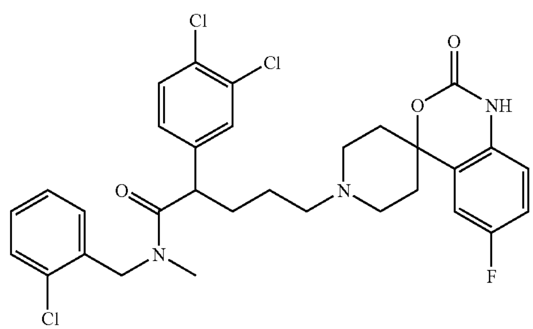 | N-(2-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (2-Chloro-benzyl)-methyl-amine (commercially available) | 618.3 |
| 116 | 590.54 | 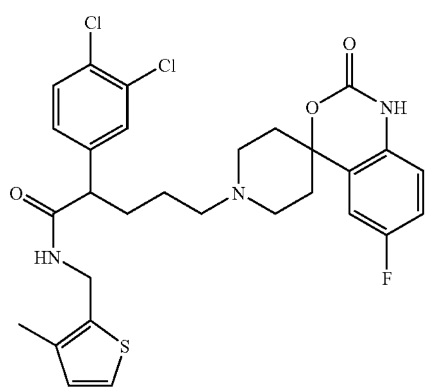 | 2-(3,4-dichlorophenyl)-5-(6-fluoro-2-oxo-1,2-dihydro-1'H-spiro[3,1-benzoxazine-4,4'-piperidin]-1'-yl)-N-[(3-methyl-2-thienyl)methyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and C-(3-Methyl-thiophen-2-yl)-methylamine (commercially available) | 590.2 |
| 117 | 598.55 | 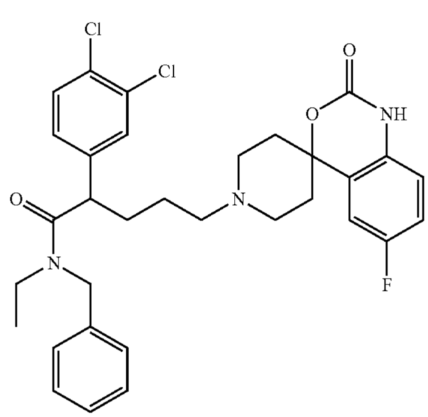 | N-benzyl-2-(3,4-dichlorophenyl)-N-ethyl-5-(6-fluoro-2-oxo-1,2-dihydro-1'H-spiro[3,1-benzoxazine-4,4'-piperidin]-1'-yl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Benzyl-ethyl-amine (commercially available) | 598.3 |

TABLE 2-continued

| Exp | MW | Structure | Compound name | Starting materials | MW found MH+ |
|---|---|---|---|---|---|
| 118 | 654.49 | 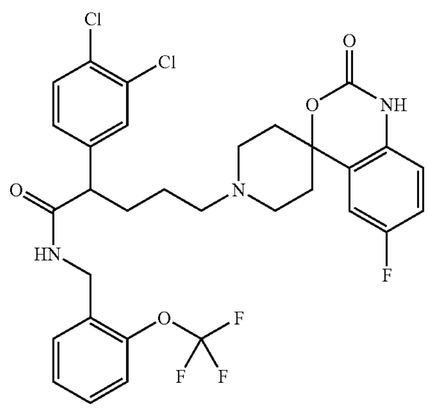 | 2-(3,4-dichlorophenyl)-5-(6-fluoro-2-oxo-1,2-dihydro-1'H-spiro[3,1-benzoxazine-4,4'-piperidin]-1'-yl)-N-[2-(trifluoromethoxy)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Trifluoromethoxy-benzylamine (commercially available) | 654.3 |
| 119 | 636.5 | 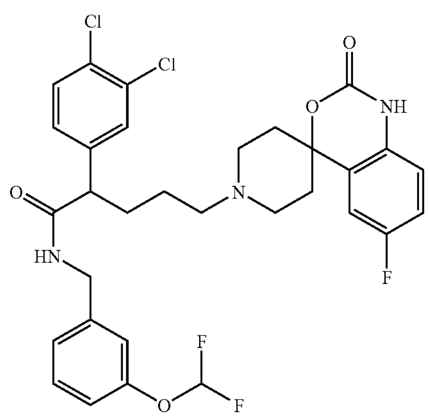 | 2-(3,4-dichlorophenyl)-N-[3-(difluoromethoxy)benzyl]-5-(6-fluoro-2-oxo 1,2-dihydro-1'H-spiro[3,1-benzoxazine-4,4'-piperidin]-1'-yl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 3-Difluoromethoxy-benzylamine (commercially available) | 636.2 |
| 120 | 618.96 | 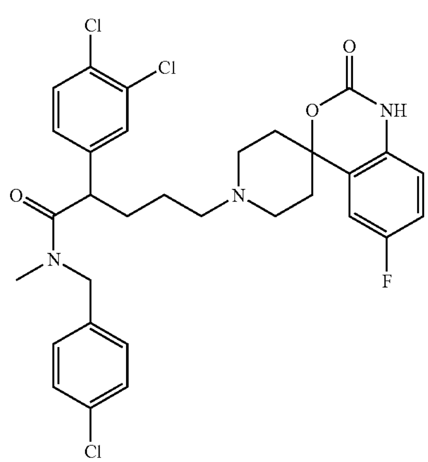 | N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (4-Chloro-benzyl)-methyl-amine (commercially available) | 618.3 |

TABLE 2-continued

| Exp | MW | Structure | Compound name | Starting materials | MW found MH+ |
|---|---|---|---|---|---|
| 121 | 652.52 | 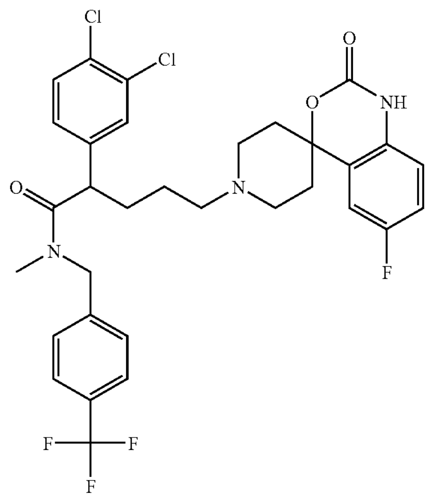 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Methyl-(4-trifluoromethyl-benzyl)-amine (commercially available) | 652.2 |
| 122 | 618.96 | 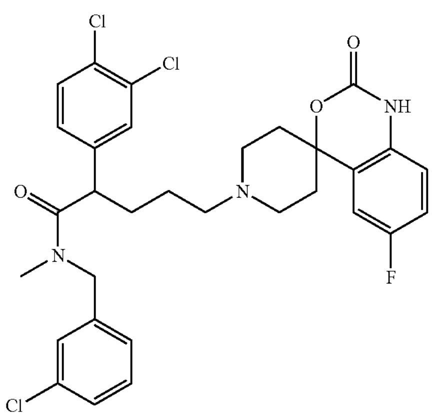 | N-(3-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (3-Chloro-benzyl)-methyl-amine (commercially available) | 618.3 |
| 123 | 667.65 | 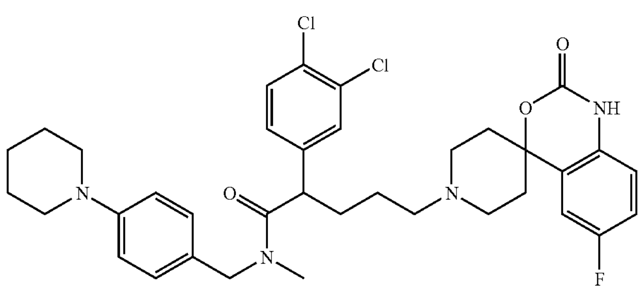 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-piperidin-1-ylbenzyl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Methyl-(4-piperidin-1-yl-benzyl)-amine (commercially available) | 667.3 |
| 124 | 661.6 | 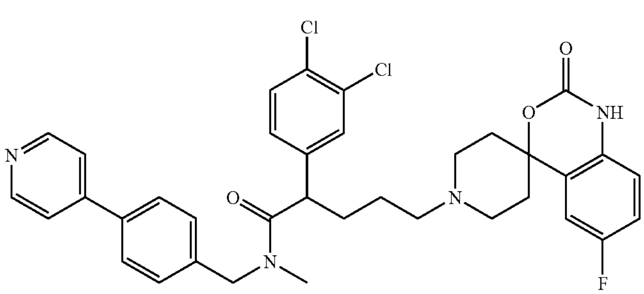 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-pyridin-4-ylbenzyl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Methyl-(4-pyridin-4-yl-benzyl)-amine (commercially available) | 661.3 |

TABLE 2-continued

| Exp | MW | Structure | Compound name | Starting materials | MW found MH+ |
|---|---|---|---|---|---|
| 125 | 604.94 | 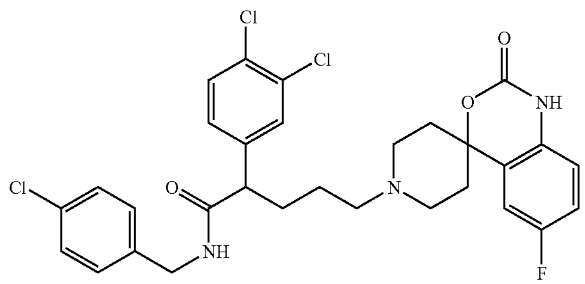 | N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Chloro-benzylamine (commercially available) | 604.3 |
| 126 | 632.53 | 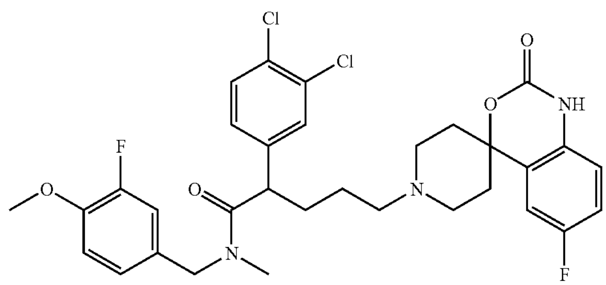 | 2-(3,4-dichlorophenyl)-N-(3-fluoro-4-methoxybenzyl)-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (3-Fluoro-4-methoxy-benzyl)-methyl-amine (commercially available) | 632.4 |
| 127 | 680.55 | 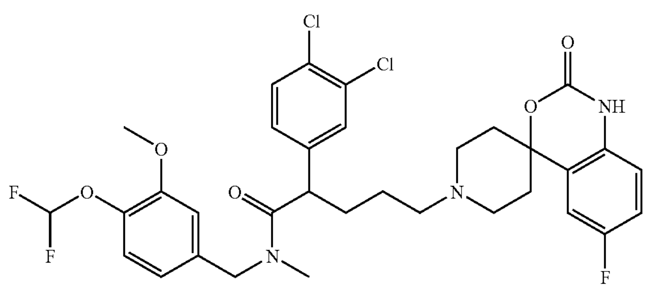 | 2-(3,4-dichlorophenyl)-N-[4-(difluoromethoxy)-3-methoxybenzyl]-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (4-Difluoro-methoxy-3-methoxy-benzyl)-methyl-amine (commercially available) | 680.3 |
| 128 | 602.51 | 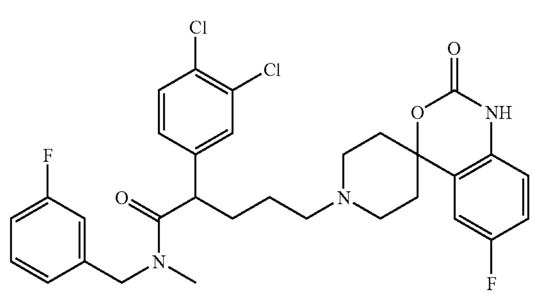 | 2-(3,4-dichlorophenyl)-N-(3-fluorobenzyl)-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (3-Fluoro-benzyl)-methyl-amine (commercially available) | 602.3 |

TABLE 2-continued

| Exp | MW | Structure | Compound name | Starting materials | MW found MH+ |
|---|---|---|---|---|---|
| 129 | 654.49 | 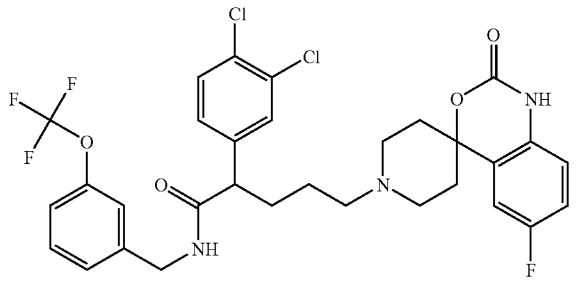 | 2-(3,4-dichlorophenyl)-5-(6-fluoro-2-oxo-1,2-dihydro-1'H-spiro[3,1-benzoxazine-4,4'-piperidin]-1'-yl)-N-[3-(trifluoromethoxy)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 3-Trifluoromethoxy-benzylamine (commercially available) | 654.4 |
| 130 | 652.52 | 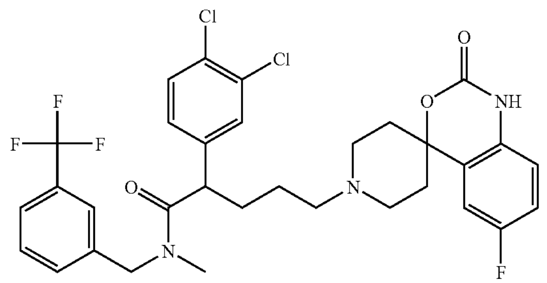 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethoxy)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Methyl-(3-trifluoromethyl-benzyl)-amine (commercially available) | 652.3 |
| 131 | 602.51 | 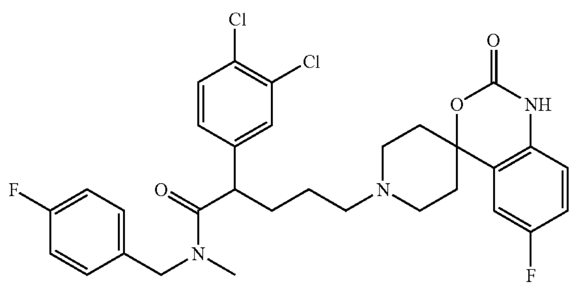 | 2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (4.Fluoro-benzyl)-methyl-amine (commercially available) | 602.3 |
| 132 | 588.48 | 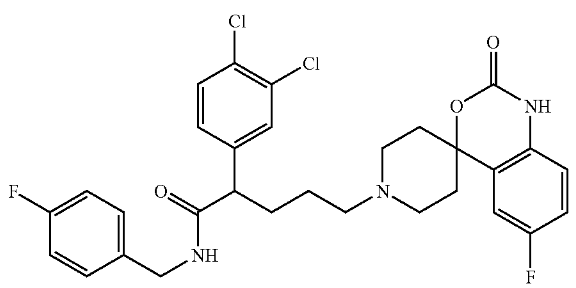 | 2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Fluoro-benzylamine (commercially available) | 588.1 |
| 133 | 600.52 | 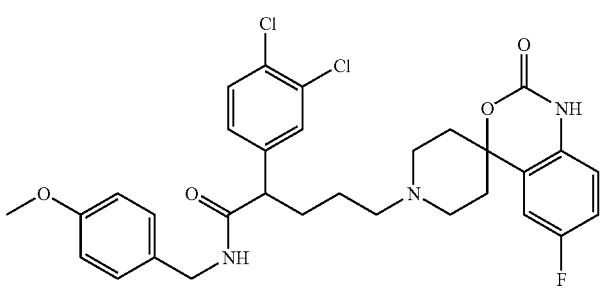 | 2-(3,4-dichlorophenyl)-5-(6-fluoro-2-oxo-1,2-dihydro-1'H-spiro[3,1-benzoxazine-4,4'-piperidin]-1'-yl)-N-(4-methoxybenzyl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Methoxy-benzylamine (commercially available) | 600.2 |

TABLE 2-continued

| Exp | MW | Structure | Compound name | Starting materials | MW found MH+ |
|---|---|---|---|---|---|
| 134 | 584.52 | 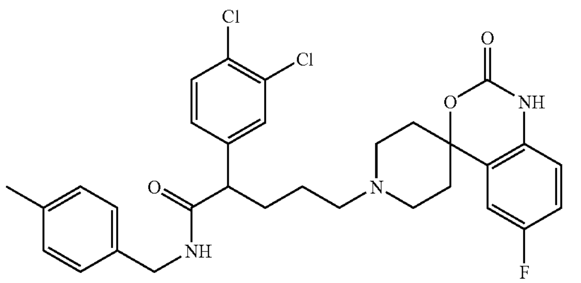 | 2-(3,4-dichlorophenyl)-5-(6-fluoro-2-oxo-1,2-dihydro-1'H-spiro[3,1-benzoxazine-4,4'-piperidin]-1'-yl)-N-(4-methylbenzyl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Methyl-benzylamine (commercially available) | 584.2 |
| 135 | 638.49 | 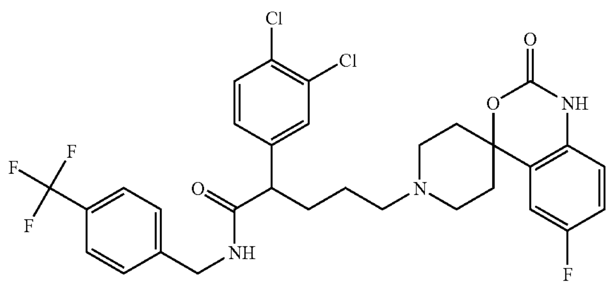 | 2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethyl)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Trifluoromethyl-benzylamine (commercially available) | 638.3 |
| 136 | 654.59 | 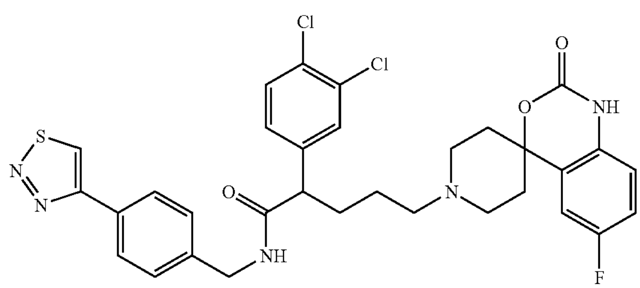 | 2-(3,4-dichlorophenyl)-5-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-[1,2,3]Thiadiazol-4-yl-benzylamine (commercially available) | 654.4 |
| 137 | 654.49 | 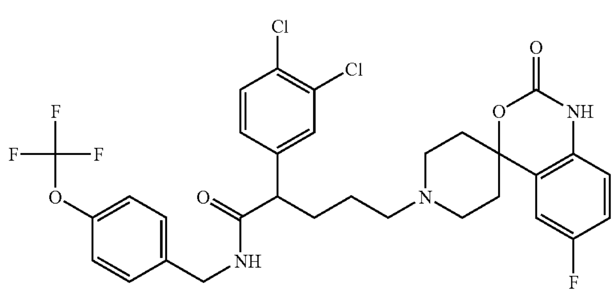 | 2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethoxy)benzyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Trifluoromethoxy-benzylamine (commercially available) | 654.3 |

TABLE 2-continued

| Exp | MW | Structure | Compound name | Starting materials | MW found MH+ |
|---|---|---|---|---|---|
| 138 | 598.55 | 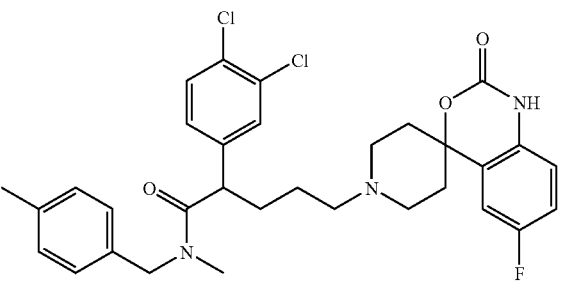 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Methyl-(4-methyl-benzyl)-amine (commercially available) | 598.3 |
| 139 | 614.52 | 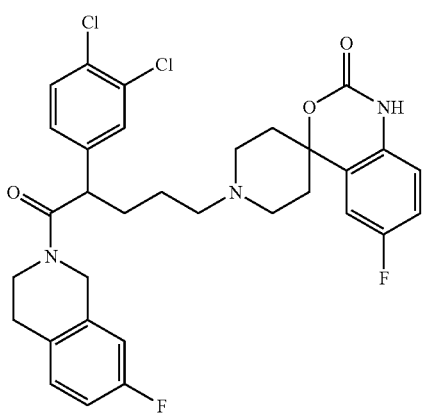 | 1'-[4-(3,4-dichlorophenyl)-5-(7-fluoro-3,4-dihydroisoquinolin-2(1H)-yl)-5-oxopentyl]-6-fluorospiro[3,1-benzoxazine-4,4'-piperidin]-2(1H)-one | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 7-Fluoro-1,2,3,4-tetrahydro-isoquinoline (commercially available) | 614.1 |
| 140 | 574.48 | 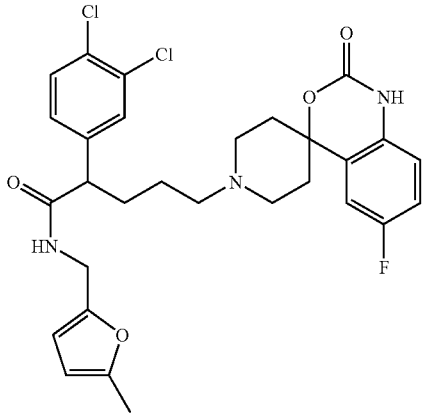 | 2-(3,4-dichlorophenyl)-5-(6-fluoro-2-oxo-1,2-dihydro-1'H-spiro[3,1-benzoxazine-4,4'-piperidin]-1'-yl)-N-[(5-methyl-2-furyl)methyl]pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and C-(5-Methyl-furan-2-yl)-methylamine (commercially available) | 576.3 |
| 141 | 598.55 | 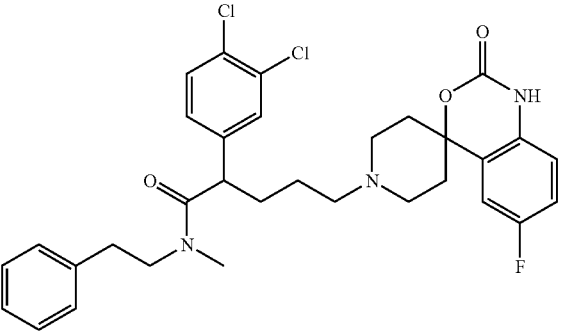 | 2-(3,4-dichlorophenyl)-5-(6-fluoro-2-oxo-1,2-dihydro-1'H-spiro[3,1-benzoxazine-4,4'-piperidin]-1'-yl)-N-methyl-N-(2-phenylethyl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and Methyl-phenethyl-amine (commercially available) | 598.3 |

TABLE 2-continued

| Exp | MW | Structure | Compound name | Starting materials | MW found MH+ |
|---|---|---|---|---|---|
| 142 | 595.5 | 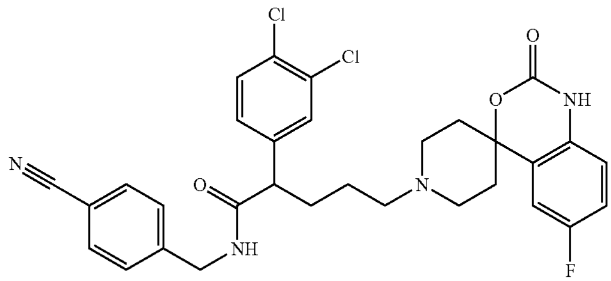 | N-(4-cyanobenzyl)-2-(3,4-dichlorophenyl)-5-(6-fluoro-2-oxo-1,2-dihydro-1'H-spiro[3,1-benzoxazine-4,4'-piperidin]-1'-yl)pentanamide | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and 4-Aminomethyl-benzonitrile (commercially available) | 595.3 |
| 143 | 606.95 | 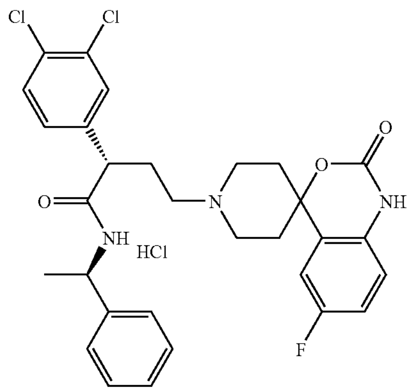 | (2S)-2-(3,4-dichlorophenyl)-4-(6-fluoro-2-oxo-1,2-dihydro-1'H-spiro[3,1-benzoxazine-4,4'-piperidin]-1'-yl)-N-[(1R)-1-phenylethyl]butanamide hydrochloride | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (R)-1-Phenyl-ethylamine (commercially available) | |
| 144 | 606.95 | 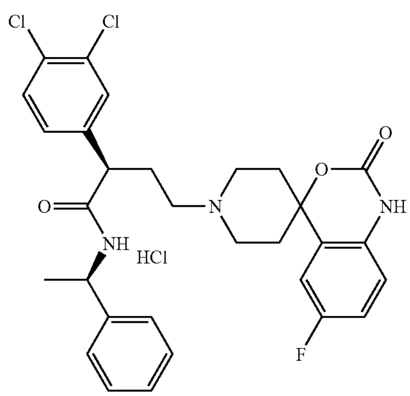 | (2R)-2-(3,4-dichlorophenyl)-4-(6-fluoro-2-oxo-1,2-dihydro-1'H-spiro[3,1-benzoxazine-4,4'-piperidin]-1'-yl)-N-[(1R)-1-phenylethyl]butanamide hydrochloride | 2-(3,4-dichlorophenyl)-5-(6-fluoro-2-oxo-1,2-dihydro-1'H-spiro[3,1-benzoxazine-4,4'-piperidin]-1'-yl)pentanoic acid, hydrochloride (intermediate 6) and (R)-1-Phenyl-ethylamine (commercially available) | |
| 145 | 606.95 | 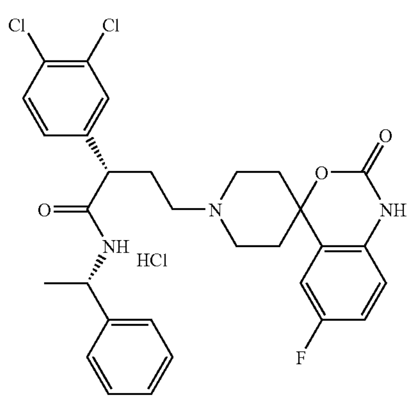 | (2S)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (S)-1-Phenyl-ethylamine (commercially available) | 570.3 |

TABLE 2-continued

| Exp | MW | Structure | Compound name | Starting materials | MW found MH+ |
|---|---|---|---|---|---|
| 146 | 606.95 | 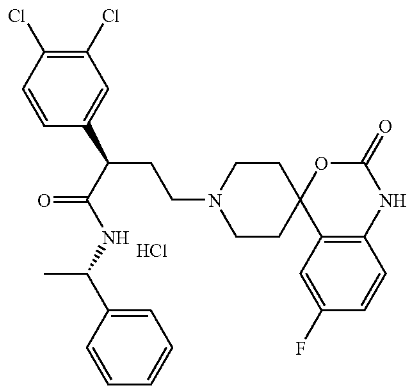 | (2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride | 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride (intermediate 3) and (S)-1-Phenyl-ethylamine (commercially available) | 570.3 |
| 147 | 618.961 | 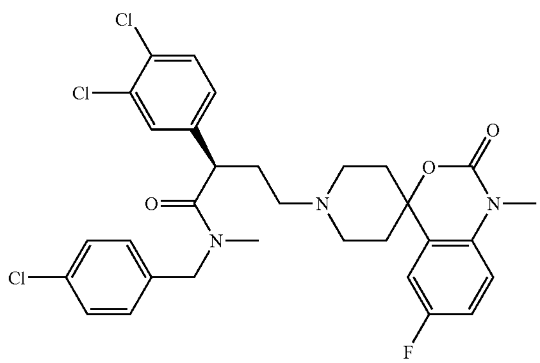 | (2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (4-Fluoro-benzyl)-methyl-amine (commercially available) | 618.3 |
| 148 | 618.961 | 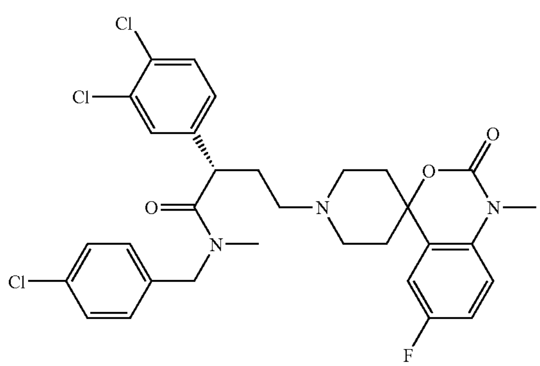 | (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide | 2-(3,4-dichlorophenyl)-4-(6-fluoro-1-methyl-2-oxo-1,2-dihydro-1'H-spiro[3,1-benzoxazine-4,4'-piperidin]-1'-yl)butanoic acid, hydrochloride (intermediate 5) and (4-Chloro-benzyl)-methyl-amine (commercially available) | 618.3 |

EXAMPLE 149

2-(3,4-dichlorophenyl)-4-(6-fluoro-2-oxo-1,2-dihydro-1'H-spiro[3,1-benzoxazine-4,4'-piperidin]-1'-yl)-N-[(1R)-2-hydroxy-1-phenylethyl]butanamide hydrochloride

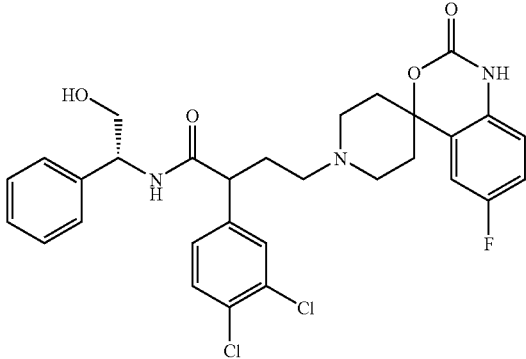

In analogy to the coupling procedure described for example 1, step 5, the title compound was prepared from 2-(3,4-dichlorophenyl)-4-(6-fluoro-2-oxo-1,2-dihydro-1'H-spiro[3,1-benzoxazine-4,4'-piperidin]-1'-yl)butanoic acid, hydrochloride and S-2-amino-2-phenyl ethanol (commercially available) and subsequent subjection to purification by flash chromatography (2% MeOH/CH$_2$Cl$_2$). The combined product fractions were evaporated to yield the title compound. MS (m/e): 516 (MH$^+$).

EXAMPLE 150

4-(6-fluoro-2-oxo-1,2-dihydro-1'H-spiro[3,1-benzoxazine-4,4'-piperidin]-1'-yl)-2-(4-fluorophenyl)-N-[(1R)-1-(hydroxymethyl)-3-methylbutyl]butanamide

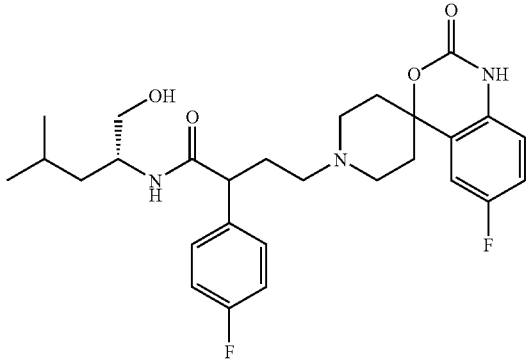

In analogy to the coupling procedure described for example 1, step 5, the title compound was prepared from 2-(4-fluoro)-4-(6-fluoro-2-oxo-1,2-dihydro-1'H-spiro[3,1-benzoxazine-4,4'-piperidin]-1'-yl)butanoic acid, hydrochloride and (R)-4-methyl-2-amino-pentanol (commercially available) and subsequent subjection to purification by flash chromatography (2% MeOH/CH$_2$Cl$_2$) to yield two diastereomers. The combined product fractions of each were evaporated to yield the title compounds. Both showed MS (m/e): 516 (MH$^+$).

EXAMPLE 151

4-(6-fluoro-2-oxo-1,2-dihydro-1'H-spiro[3,1-benzoxazine-4,4'-piperidin]-1'-yl)-2-(4-fluorophenyl)-N-[(1R)-2-hydroxy-1-phenylethyl]butanamide

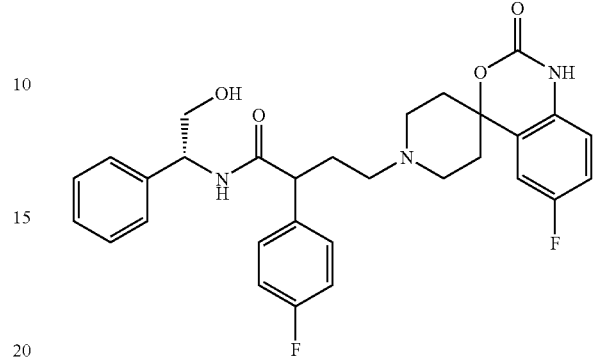

In analogy to the coupling procedure described for example 1, step 5, the title compound was prepared from 2-(4-fluorophenyl)-4-(6-fluoro-2-oxo-1,2-dihydro-1'H-spiro[3,1-benzoxazine-4,4'-piperidin]-1'-yl)butanoic acid, hydrochloride and (R)-2-amino-2-phenyl ethanol (commercially available) and subsequent subjection to purification by flash chromatography (2% MeOH/CH$_2$Cl$_2$). The diastereomers were separated in this way and each of the combined product fractions were evaporated to yield the title compound. MS (m/e): 536 (MH$^+$).

The invention claimed is:
1. A compound of formula

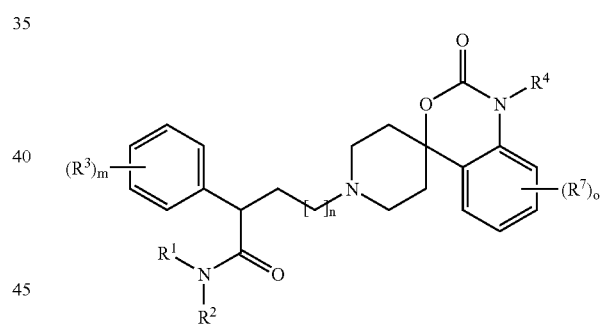

I wherein
$R^1$ is hydrogen or lower alkyl;
$R^2$ is lower alkyl, lower hydroxyalkyl or —(CHR$^5$)$_x$-A;
  $R^5$ is hydrogen, lower alkyl, lower hydroxyalkyl, or heteroaryl optionally substituted by lower alkyl;
  A is a cycloalkyl, aryl, heterocyclyl or heteroaryl ring, which rings are optionally substituted by one or more $R^6$, wherein $R^6$ is lower alkyl, lower alkoxy, lower alkylsulfonyl, cyano, halogen, lower alkyl substituted by halogen or lower alkoxy substituted by halogen, or is aryl, heterocyclyl or heteroaryl optionally substituted by lower alkyl or is cycloalkyl optionally substituted by lower alkyl;
  x is 0, 1, 2 or 3;
or $R^1$ and $R^2$ together with the N-atom to which they are attached form a heterocyclyl or heteroaryl ring, which rings are optionally substituted by one or more substituents selected from the group consisting of lower alkyl, lower alkoxy, lower alkylsulfonyl, halogen, cycloalkyl, benzyl and aryl;

$R^3$ is hydrogen or halogen;

$R^4$ is hydrogen or lower alkyl;

$R^7$ is hydrogen, halogen or lower alkyl;

m is 1 or 2; when m is 2, each $R^3$ can be the same or different;

n is 1 or 2;

o is 1 or 2; when o is 2, each $R^7$ can be the same or different;

or a pharmaceutically suitable acid addition salt thereof.

2. A compound of claim 1, wherein one of $R^1$ or $R^2$ is lower alkyl.

3. A compound of claim 2, selected from the group consisting of

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide; and N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide.

4. A compound of claim 2, selected from the group consisting of 2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide; and 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide.

5. A compound of claim 2, selected from the group consisting of 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide; and 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide.

6. A compound of claim 2, selected from the group consisting of 2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

7. A compound of claim 1, wherein one of $R^1$ or $R^2$ represents $-(CHR^5)_x-A$, where A is aryl or heteroaryl and x is 1.

8. A compound of claim 7, selected from the group consisting of

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(4-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide; and 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide.

9. A compound of claim 7, selected from the group consisting of

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-4-(6-fluoro-2-oxo-1,2-dihydro-1'H-spiro[3,1-benzoxazine-4,4'-piperidin]-1'-yl)-2-(4-fluorophenyl)butanamide;

4-(6-fluoro-2-oxo-1,2-dihydro-1'H-spiro[3,1-benzoxazine-4,4'-piperidin]-1'-yl)-2-(4-fluorophenyl)-N-[2-(trifluoromethoxy)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

4-(6-fluoro-2-oxo-1,2-dihydro-1'H-spiro[3,1-benzoxazine-4,4'-piperidin]-1'-yl)-2-(4-fluorophenyl)-N-[3-(trifluoromethyl)benzyl]butanamide;

N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide; and 2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide.

10. A compound of claim 7, selected from the group consisting of 2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide; and N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide.

11. A compound of claim 7, selected from the group consisting of

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide; and 2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide.

12. A compound of claim 7, selected from the group consisting of 2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-5-(6-fluoro-2-oxo-1,2-dihydro-1'H-spiro[3,1-benzoxazine-4,4'-piperidin]-1'-yl)-N-[(3-methyl-2-thienyl)methyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-[2-(trifluoromethoxy)benzyl]pentanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)pentanamide;

2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethyl)benzyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide;

(2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

13. A compound of claim 1, wherein $R^1$ and $R^2$ together with the N-atom to which they are attached form a heterocyclyl or heteroaryl ring, which rings are substituted by one or more halogen atoms.

14. A compound of claim 13, selected from the group consisting of

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one; and 1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one.

15. A compound of claim 1, wherein $R^3$ is chlorine and m is 2.

16. A compound of claim 15, selected from the group consisting of

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one; and 2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide.

17. A compound of claim 15, selected from the group consisting of

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide; and 2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide.

18. A compound of claim 15, selected from the group consisting of 2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide; and 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide.

19. A compound of claim 15, selected from the group consisting of 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-5-(6-fluoro-2-oxo-1,2-dihydro-1'H-spiro[3,1-benzoxazine-4,4'-piperidin]-1'-yl)-N-[(3-methyl-2-thienyl)methyl]pentanamide; and 2-(3,4-dichlorophenyl)-5-(6-fluoro-2-oxo-1,2-dihydro-1'H-spiro[3,1-benzoxazine-4,4'-piperidin]-1'-yl)-N-[2-(trifluoromethoxy)benzyl]pentanamide.

20. A compound of claim 15, selected from the group consisting of

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[4-(trifluoromethyl)benzyl]pentanamide;

N-(4-chlorobenzyl)-2-(3,4-dichlorophenyl)-5-(6-fluoro-2-oxo-1,2-dihydro-1'H-spiro[3,1-benzoxazine-4,4'-piperidin]-1'-yl)pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-[3-(trifluoromethyl)benzyl]pentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)-N-methylpentanamide;

2-(3,4-dichlorophenyl)-N-(4-fluorobenzyl)-5-(6-fluoro-2-oxo-1,2-dihydro-1'H-spiro[3,1-benzoxazine-4,4'-piperidin]-1'-yl)pentanamide;

2-(3,4-dichlorophenyl)-5-(6-fluoro-2-oxo-1,2-dihydro-1'H-spiro[3,1-benzoxazine-4,4'-piperidin]-1'-yl)-N-[4-(trifluoromethyl)benzyl]pentanamide;

2-(3,4-dichlorophenyl)-5-(6-fluoro-2-oxo-1,2-dihydro-1'H-spiro[3,1-benzoxazine-4,4'-piperidin]-1'-yl)-N-methyl-N-(4-methylbenzyl)pentanamide;

(2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

21. A compound of claim 1, wherein $R^4$ is lower alkyl.

22. A compound of claim 21, selected from the group consisting of

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

1'-[3-(3,4-dichlorophenyl)-4-(7-fluoro-3,4-dihydroisoquinolin-2(1H)-yl)-4-oxobutyl]-6-fluoro-1-methyl-spiro[3,1-benzoxazine-4,4'-piperidin]-2(1H)-one;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide.

23. A compound of claim 21, selected from the group consisting of

N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide; and 2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide.

24. A compound of claim 21, selected from the group consisting of 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

25. A compound of claim 1, wherein n is 1.

26. A compound of claim 25, selected from the group consisting of

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide hydrochloride;

N-benzyl-2-(3,4-dichlorophenyl)-N-ethyl-4-(6-fluoro-2-oxo-1,2-dihydro-1'H-spiro[3,1-benzoxazine-4,4'-piperidin]-1'-yl)butanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[(5-methyl-2-furyl)methyl]butanamide;

2-(3,4-dichlorophenyl)-N-ethyl-N-(2-fluorobenzyl)-4-(6-fluoro-2-oxo-1,2-dihydro-1'H-spiro[3,1-benzoxazine-4,4'-piperidin]-1'-yl)butanamide;

N-butyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(2-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-ethyl-4-(6-fluoro-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

N-(3-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-(2-chlorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide;

N-benzyl-2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)butanamide; and 2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methylbenzyl)butanamide.

27. A compound of claim 25, selected from the group consisting of

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(methylsulfonyl)benzyl]butanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

1'-[3-(3,4-dichlorophenyl)-4-(7-fluoro-3,4-dihydroisoquinolin-2(1H)-yl)-4-oxobutyl]-6-fluoro-1-methylspiro[3,1-benzoxazine-4,4'-piperidin]-2(1H)-one;

2-(3,4-dichlorophenyl)-N-ethyl-4-(6-fluoro-1-methyl-2-oxo-1,2-dihydro-1'H-spiro[3,1-benzoxazine-4,4'-piperidin]-1'-yl)-N-(4-methylbenzyl)butanamide;

N-(3-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

1'-[3-(3,4-dichlorophenyl)-4-(4-fluoropiperidin-1-yl)-4-oxobutyl]-6-fluoro-1-methylspiro[3,1-benzoxazine-4,4'-piperidin]-2(1H)-one;

N-(2-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

N-(2,4-dichlorobenzyl)-4-(6-fluoro-2-oxo-1,2-dihydro-1'H-spiro[3,1-benzoxazine-4,4'-piperidin]-1'-yl)-2-(4-fluorophenyl)butanamide;

4-(6-fluoro-2-oxo-1,2-dihydro-1'H-spiro[3,1-benzoxazine-4,4'-piperidin]-1'-yl)-2-(4-fluorophenyl)-N-[2-(trifluoromethoxy)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[4-(trifluoromethyl)benzyl]butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-(4-methylbenzyl)butanamide;

4-(6-fluoro-2-oxo-1,2-dihydro-1'H-spiro[3,1-benzoxazine-4,4'-piperidin]-1'-yl)-2-(4-fluorophenyl)-N-methyl-N-[3-(trifluoromethyl)benzyl]butanamide;

N-(4-fluorobenzyl)-4-(6-fluoro-2-oxo-1,2-dihydro-1'H-spiro[3,1-benzoxazine-4,4'-piperidin]-1'-yl)-2-(4-fluorophenyl)-N-methylbutanamide; and 4-(6-fluoro-2-oxo-1,2-dihydro-1'H-spiro[3,1-benzoxazine-4,4'-piperidin]-1'-yl)-2-(4-fluorophenyl)-N-[3-(trifluoromethyl)benzyl]butanamide.

28. A compound of claim 25, selected from the group consisting of

N-(2,4-dichlorobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-morpholin-4-ylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-pyridin-4-ylbenzyl)butanamide;

2-(3,4-dichlorophenyl)-N-(3-fluoro-4-methoxybenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-methyl-N-[3-(trifluoromethyl)benzyl]butanamide; and 2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)-N-methylbutanamide.

29. A compound of claim 25, selected from the group consisting of 2-(3,4-dichlorophenyl)-N-(4-fluorobenzyl)-4-(6-fluoro-2-oxo-1,2-dihydro-1'H-spiro[3,1-benzoxazine-4,4'-piperidin]-1'-yl)butanamide;

2-(3,4-dichlorophenyl)-4-(6-fluoro-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-2-oxo-1,2-dihydro-1'H-spiro[3,1-benzoxazine-4,4'-piperidin]-1'-yl)butanamide;

N-(2,4-dichlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-[(4-chlorophenyl)(1-methyl-1H-imidazol-2-yl)methyl]-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

N-benzyl-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(2-phenylethyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[2-(trifluoromethoxy)benzyl]butanamide;

2-(3,4-dichlorophenyl)-N-[3-(difluoromethoxy)benzyl]-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[4-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1H-pyrazol-1-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-morpholin-4-ylbenzyl)butanamide; and 2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-pyridin-4-ylbenzyl)butanamide.

30. A compound of claim 25, selected from the group consisting of 2-(3,4-dichlorophenyl)-N-(3-fluoro-4-methoxybenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-[4-(difluoromethoxy)-3-methoxybenzyl]-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(3-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-(4-methylbenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethoxy)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-methyl-N-[3-(trifluoromethyl)benzyl]butanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)-N-methylbutanamide;

2-(3,4-dichlorophenyl)-N-(4-fluorobenzyl)-4-(6-fluoro-1-methyl-2-oxo-1,2-dihydro-1'H-spiro[3,1-benzoxazine-4,4'-piperidin]-1'-yl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-(4-methoxybenzyl)butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[3-(trifluoromethyl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(1,2,3-thiadiazol-4-yl)benzyl]butanamide;

2-(3,4-dichlorophenyl)-4-(6-fluoro-1-methyl-2-oxo-1,2-dihydro-1'H-spiro[3,1-benzoxazine-4,4'-piperidin]-1'-yl)-N-[4-(trifluoromethoxy)benzyl]butanamide;

N-(4-cyanobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)butanamide;

(2R)-2-(3,4-dichlorophenyl)-4-(6-fluoro-2-oxo-1,2-dihydro-1'H-spiro[3,1-benzoxazine-4,4'-piperidin]-1'-yl)-N-[(1S)-1-phenylethyl]butanamide hydrochloride;

(2R)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide; and (2S)-N-(4-chlorobenzyl)-2-(3,4-dichlorophenyl)-4-(6-fluoro-1-methyl-2-oxo-1,2-dihydro-1'H-spiro[3,1-benzoxazine-4,4'-piperidin]-1'-yl)-N-methylbutanamide.

31. A pharmaceutical composition comprising a therapeutically effective amount of a compound of formula I

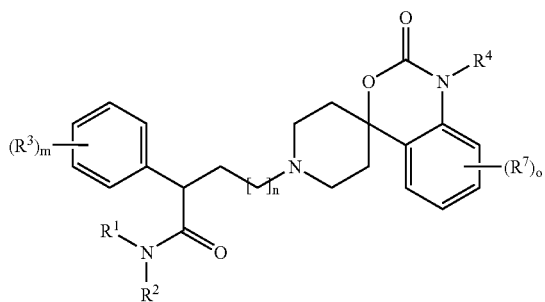

wherein $R^1$ is hydrogen or lower alkyl;

$R^2$ is lower alkyl, lower hydroxyalkyl or —$(CHR^5)_x$-A;

$R^5$ is hydrogen, lower alkyl, lower hydroxyalkyl, or heteroaryl optionally substituted by lower alkyl;

A is a cycloalkyl, aryl, heterocyclyl or heteroaryl ring, which rings are optionally substituted by one or more $R^6$, wherein $R^6$ is lower alkyl, lower alkoxy, lower alkylsulfonyl, cyano, halogen, lower alkyl substituted by halogen or lower alkoxy substituted by halogen, or is aryl, heterocyclyl or heteroaryl optionally substituted by lower alkyl or is cycloalkyl optionally substituted by lower alkyl;

x is 0, 1, 2 or 3;

or $R^1$ and $R^2$ together with the N-atom to which they are attached form a heterocyclyl or heteroaryl ring, which rings are optionally substituted by one or more substituents selected from the group consisting of lower alkyl, lower alkoxy, lower alkylsulfonyl, halogen, cycloalkyl, benzyl and aryl;

$R^3$ is hydrogen or halogen;

$R^4$ is hydrogen or lower alkyl;

$R^7$ is hydrogen, halogen or lower alkyl;

m is 1 or 2; when m is 2, each $R^3$ can be the same or different;

n is 1 or 2;

o is 1 or 2; when o is 2, each $R^7$ can be the same or different;

or a pharmaceutically suitable acid addition salt thereof and a pharmaceutically acceptable carrier.

* * * * *